United States Patent
Nicholas et al.

(10) Patent No.: US 10,261,850 B2
(45) Date of Patent: Apr. 16, 2019

(54) AGGREGATE PREDICTIVE MODEL AND WORKFLOW FOR LOCAL EXECUTION

(71) Applicant: Uptake Technologies, Inc., Chicago, IL (US)

(72) Inventors: Brad Nicholas, Wheaton, IL (US); Jason Kolb, Plainfield, IL (US)

(73) Assignee: Uptake Technologies, Inc., Chicago, IL (US)

( * ) Notice: Subject to any disclaimer, the term of this patent is extended or adjusted under 35 U.S.C. 154(b) by 811 days.

(21) Appl. No.: 14/744,352

(22) Filed: Jun. 19, 2015

(65) Prior Publication Data
US 2016/0371599 A1 Dec. 22, 2016

(51) Int. Cl.
*G06F 11/07* (2006.01)
*G06N 5/04* (2006.01)
(Continued)

(52) U.S. Cl.
CPC ............ *G06F 11/079* (2013.01); *G01D 3/08* (2013.01); *G01M 99/008* (2013.01); *G06F 11/008* (2013.01); *G06F 11/0709* (2013.01); *G06F 11/0721* (2013.01); *G06F 11/0751* (2013.01); *G06F 11/0772* (2013.01); *G06F 11/0787* (2013.01); *G06F 11/0793* (2013.01); *G06F 11/2007* (2013.01); *G06F 11/26* (2013.01); *G06F 11/263* (2013.01); *G06N 5/02* (2013.01); *G06N 5/04* (2013.01); *G06N 7/005* (2013.01); *G06Q 10/04* (2013.01); *G06Q 10/067* (2013.01); *G06Q 10/06312* (2013.01); *G06Q 10/20* (2013.01); *G08B 21/18* (2013.01); *H04L 45/22* (2013.01); *G06F 2201/85* (2013.01)

(58) Field of Classification Search
CPC ............ G06N 5/02; G06N 7/00; G06F 11/07
See application file for complete search history.

(56) References Cited

U.S. PATENT DOCUMENTS 5,566,092 A  10/1996  Wang et al.
5,633,800 A   5/1997  Bankert et al.
(Continued)

FOREIGN PATENT DOCUMENTS

EP    1403437       12/2013
JP    2009206850     9/2009
(Continued)

OTHER PUBLICATIONS

Duan, Rubing, Radu Prodan, and Thomas Fahringer. "Short paper: Data mining-based fault prediction and detection on the grid." High Performance Distributed Computing, 2006 15th IEEE International Symposium on. IEEE, 2006.*
(Continued)

*Primary Examiner* — Eric Nilsson
(74) *Attorney, Agent, or Firm* — Lee Sullivan Shea & Smith LLP

(57) ABSTRACT

Disclosed herein are systems, devices, and methods related to assets and predictive models and corresponding workflows that are related to the operation of assets. In particular, examples involve defining and deploying aggregate, predictive models and corresponding workflows, defining and deploying individualized, predictive models and/or corresponding workflows, and dynamically adjusting the execution of model-workflow pairs.

20 Claims, 17 Drawing Sheets

(51) Int. Cl.

| | | |
|---|---|---|
| G06N 7/00 | (2006.01) | |
| G06Q 10/00 | (2012.01) | |
| G06F 11/26 | (2006.01) | |
| G06F 11/263 | (2006.01) | |
| G08B 21/18 | (2006.01) | |
| G06F 11/00 | (2006.01) | |
| G01D 3/08 | (2006.01) | |
| G01M 99/00 | (2011.01) | |
| G06F 11/20 | (2006.01) | |
| G06N 5/02 | (2006.01) | |
| H04L 12/707 | (2013.01) | |
| G06Q 10/06 | (2012.01) | |
| G06Q 10/04 | (2012.01) | |

(56) References Cited

U.S. PATENT DOCUMENTS

| | | |
|---|---|---|
| 6,256,594 B1 | 7/2001 | Yamamoto et al. |
| 6,336,065 B1 | 1/2002 | Gibson et al. |
| 6,442,542 B1 | 8/2002 | Ramani et al. |
| 6,473,659 B1 | 10/2002 | Shah et al. |
| 6,622,264 B1 | 9/2003 | Bliley et al. |
| 6,634,000 B1 | 10/2003 | Jammu et al. |
| 6,643,600 B2 | 11/2003 | Yanosik et al. |
| 6,650,949 B1 | 11/2003 | Fera et al. |
| 6,725,398 B1 | 4/2004 | Varma et al. |
| 6,760,631 B1 | 7/2004 | Berkowitz et al. |
| 6,775,641 B2 | 8/2004 | Wegerich et al. |
| 6,799,154 B1 | 9/2004 | Aragones et al. |
| 6,823,253 B2 | 11/2004 | Brunell |
| 6,859,739 B2 | 2/2005 | Wegerich et al. |
| 6,892,163 B1 | 5/2005 | Herzog et al. |
| 6,947,797 B2 | 9/2005 | Dean et al. |
| 6,952,662 B2 | 10/2005 | Wegerich et al. |
| 6,957,172 B2 | 10/2005 | Wegerich |
| 6,975,962 B2 | 12/2005 | Wegerich et al. |
| 7,020,595 B1 | 3/2006 | Adibhatla et al. |
| 7,082,379 B1 | 7/2006 | Bickford et al. |
| 7,100,084 B2 | 8/2006 | Unkle et al. |
| 7,107,491 B2 | 9/2006 | Graichen et al. |
| 7,127,371 B2 | 10/2006 | Duckert et al. |
| 7,233,886 B2 | 6/2007 | Wegerich et al. |
| 7,280,941 B2 | 10/2007 | Bonanni et al. |
| 7,308,385 B2 | 12/2007 | Wegerich et al. |
| 7,373,283 B2 | 5/2008 | Herzog et al. |
| 7,403,869 B2 | 7/2008 | Wegerich et al. |
| 7,409,320 B2 | 8/2008 | Wegerich |
| 7,415,382 B1 | 8/2008 | Bickford et al. |
| 7,428,478 B2 | 9/2008 | Aragones |
| 7,447,666 B2 | 11/2008 | Wang |
| 7,457,693 B2 | 11/2008 | Olsen et al. |
| 7,457,732 B2 | 11/2008 | Aragones et al. |
| 7,509,235 B2 | 3/2009 | Bonissone et al. |
| 7,509,537 B1 | 3/2009 | Jensen et al. |
| 7,536,364 B2 | 5/2009 | Subbu et al. |
| 7,539,597 B2 | 5/2009 | Wegerich et al. |
| 7,548,830 B2 | 6/2009 | Goebel et al. |
| 7,634,384 B2 | 12/2009 | Eryurek et al. |
| 7,640,145 B2 | 12/2009 | Wegerich et al. |
| 7,660,705 B1 | 2/2010 | Meek et al. |
| 7,693,608 B2 | 4/2010 | Nasle |
| 7,725,293 B2 | 5/2010 | Bonissone et al. |
| 7,739,096 B2 | 6/2010 | Wegerich et al. |
| 7,756,678 B2 | 7/2010 | Bonissone et al. |
| 7,783,507 B2 * | 8/2010 | Schick ............... B61L 27/0094 705/7.11 |
| 7,822,578 B2 | 10/2010 | Kasztenny et al. |
| 7,869,908 B2 | 1/2011 | Walker |
| 7,919,940 B2 | 4/2011 | Miller et al. |
| 7,941,701 B2 | 5/2011 | Wegerich et al. |
| 7,962,240 B2 | 6/2011 | Morrison et al. |
| 8,024,069 B2 | 9/2011 | Miller et al. |
| 8,050,800 B2 | 11/2011 | Miller et al. |
| 8,145,578 B2 | 3/2012 | Pershing et al. |
| 8,229,769 B1 | 7/2012 | Hopkins |
| 8,234,420 B2 | 7/2012 | Lueckenbach et al. |
| 8,239,170 B2 | 8/2012 | Wegerich |
| 8,275,577 B2 | 9/2012 | Herzog |
| 8,285,402 B2 | 10/2012 | Lueckenbach et al. |
| 8,311,774 B2 | 11/2012 | Hines |
| 8,352,216 B2 | 1/2013 | Subbu et al. |
| 8,532,795 B2 | 9/2013 | Adavi et al. |
| 8,533,018 B2 | 9/2013 | Miwa et al. |
| 8,560,494 B1 | 10/2013 | Downing et al. |
| 8,620,618 B2 | 12/2013 | Eryurek et al. |
| 8,620,853 B2 | 12/2013 | Herzog |
| 8,626,385 B2 | 1/2014 | Humphrey |
| 8,645,276 B2 | 2/2014 | Wong et al. |
| 8,660,980 B2 | 2/2014 | Herzog |
| 8,689,108 B1 | 4/2014 | Duffield et al. |
| 8,713,467 B1 | 4/2014 | Goldenberg et al. |
| 8,786,605 B1 | 7/2014 | Curtis et al. |
| 8,799,799 B1 | 8/2014 | Cervelli et al. |
| 8,812,960 B1 | 8/2014 | Sun et al. |
| 8,832,594 B1 | 9/2014 | Thompson et al. |
| 8,850,000 B2 | 9/2014 | Collins et al. |
| 8,862,938 B2 | 10/2014 | Souvannarath |
| 8,868,537 B1 | 10/2014 | Colgrove et al. |
| 8,886,601 B1 | 11/2014 | Landau et al. |
| 8,909,656 B2 | 12/2014 | Kumar et al. |
| 8,917,274 B2 | 12/2014 | Ma et al. |
| 8,918,246 B2 | 12/2014 | Friend |
| 8,924,429 B1 | 12/2014 | Fisher et al. |
| 8,935,201 B1 | 1/2015 | Fisher et al. |
| 8,937,619 B2 | 1/2015 | Sharma et al. |
| 8,938,686 B1 | 1/2015 | Erenrich et al. |
| 9,846,479 B1 | 12/2017 | Brown et al. |
| 2002/0013635 A1 | 1/2002 | Gotou et al. |
| 2002/0091972 A1 | 7/2002 | Harris et al. |
| 2002/0152056 A1 | 10/2002 | Herzog et al. |
| 2003/0055666 A1 | 3/2003 | Roddy et al. |
| 2003/0126258 A1 | 7/2003 | Conkright et al. |
| 2003/0139905 A1 | 7/2003 | Helsper et al. |
| 2004/0181712 A1 | 9/2004 | Taniguchi et al. |
| 2004/0243636 A1 | 12/2004 | Hasiewicz et al. |
| 2004/0267394 A1 | 12/2004 | Kempf et al. |
| 2005/0083196 A1 | 4/2005 | Furem et al. |
| 2005/0119905 A1 | 6/2005 | Wong et al. |
| 2005/0222747 A1 | 10/2005 | Vhora et al. |
| 2007/0067678 A1 | 3/2007 | Hosek et al. |
| 2007/0220368 A1 | 9/2007 | Jaw et al. |
| 2007/0263628 A1 | 11/2007 | Axelsson et al. |
| 2007/0266557 A1 * | 11/2007 | Drost .................. G02B 6/4226 29/834 |
| 2008/0059080 A1 | 3/2008 | Greiner et al. |
| 2008/0059120 A1 | 3/2008 | Xiao et al. |
| 2008/0221834 A1 | 9/2008 | Damodharan |
| 2008/0320151 A1 | 12/2008 | McCanne et al. |
| 2010/0228376 A1 | 9/2010 | Stafford et al. |
| 2011/0276828 A1 * | 11/2011 | Tamaki ............. G05B 23/0254 714/26 |
| 2012/0092180 A1 | 4/2012 | Rikkola et al. |
| 2012/0271612 A1 | 10/2012 | Barsoum et al. |
| 2012/0310597 A1 | 12/2012 | Uchiyama et al. |
| 2012/0316845 A1 | 12/2012 | Grey et al. |
| 2013/0010610 A1 | 1/2013 | Karthikeyan et al. |
| 2013/0024416 A1 | 1/2013 | Herzog |
| 2013/0283773 A1 | 10/2013 | Hague |
| 2013/0325502 A1 | 12/2013 | Robicsek et al. |
| 2014/0012886 A1 | 1/2014 | Downing et al. |
| 2014/0032132 A1 | 1/2014 | Stratton et al. |
| 2014/0060030 A1 | 3/2014 | Ma et al. |
| 2014/0089035 A1 | 3/2014 | Jericho et al. |
| 2014/0105481 A1 | 4/2014 | Hasselbusch et al. |
| 2014/0107828 A1 | 4/2014 | Zhu et al. |
| 2014/0121868 A1 | 5/2014 | Zhang et al. |
| 2014/0169398 A1 | 6/2014 | Arndt et al. |
| 2014/0170617 A1 | 6/2014 | Johnson et al. |
| 2014/0184643 A1 | 7/2014 | Friend |
| 2014/0188778 A1 | 7/2014 | Garvey et al. |
| 2014/0208163 A1 | 7/2014 | Domke et al. |
| 2014/0222355 A1 | 8/2014 | Cheim et al. |
| 2014/0309864 A1 | 10/2014 | Ricci |

(56) References Cited

U.S. PATENT DOCUMENTS

| | | |
|---|---|---|
| 2014/0310228 A1 | 10/2014 | Nakabayashi et al. |
| 2014/0330600 A1 | 11/2014 | Candas et al. |
| 2014/0330749 A1* | 11/2014 | Candas .................. G06Q 40/06 705/36 R |
| 2014/0351642 A1 | 11/2014 | Bates et al. |
| 2014/0357295 A1 | 12/2014 | Skomra et al. |
| 2014/0358601 A1 | 12/2014 | Smiley et al. |
| 2015/0005903 A1 | 1/2015 | Worek et al. |
| 2015/0046870 A1 | 2/2015 | Goldenberg et al. |
| 2015/0156031 A1 | 6/2015 | Fadell et al. |
| 2015/0262060 A1 | 9/2015 | Husain et al. |
| 2015/0286969 A1 | 10/2015 | Warner et al. |
| 2015/0300892 A1 | 10/2015 | Malhotra et al. |
| 2016/0018796 A1 | 1/2016 | Lu |
| 2016/0028605 A1 | 1/2016 | Gil et al. |
| 2016/0028648 A1 | 1/2016 | Wohlert et al. |
| 2016/0261115 A1 | 9/2016 | Asati et al. |
| 2016/0343093 A1 | 11/2016 | Riland et al. |
| 2016/0349330 A1* | 12/2016 | Barfield, Jr. ......... G07C 5/0816 |

FOREIGN PATENT DOCUMENTS

| | | |
|---|---|---|
| KR | 10-2010-0074833 | 7/2010 |
| KR | 10-2010-0076708 | 7/2010 |
| WO | 2011117570 | 9/2011 |
| WO | 2012103290 A1 | 8/2012 |
| WO | 2013034420 | 3/2013 |
| WO | 2014145977 | 9/2014 |
| WO | 2014205497 | 12/2014 |

OTHER PUBLICATIONS

International Searching Authority, Written Opinion dated Sep. 20, 2016, issued in connection with International Application No. PCT/US2016/037247, filed on Jun. 13, 2016, 13 pages.

International Searching Authority, Written Opinion dated Sep. 20, 2016, issued in connection with International Application No. PCT/US2016/038261, filed on Jun. 18, 2016, 7 pages.

"International Search Report for Application No. PCT/US2016/037247, dated Sep. 20, 2016, 3 pages".

"International Search Report for Application No. PCT/US2016/038261, dated Sep. 20, 2016, 3 pages".

Biswas, "Redundancy-based Approaches in Wireless Multihop Network Design", PhD Dissertation Submitted to Graduate Faculty of North Carolina State University (2014).

Isermann, "Model-based Fault Detection and Diagnosis—Status and Applications", Institute of Automatic Control, Darmstadt University of Technology (2004).

Narasimhan et al, "Combining Model-Based and Feature-Driven Diagnosis Approaches—A Case Study on Electromechanical Actuators", 21st International Workshop on Principles of Diagnosis (2010).

Prentzas et al, Categorizing Approaches Combining Rule-Based and Case-Based Reasoning.

Infor M3 Enterprise Management System, Infor.com (2014).

Infor Equipment, Infor.com (2012).

Infor Introduces Next-Generation Solution for Equipment Dealers and Service Providers, Infor.com (Feb. 20, 2014).

Infor Equipment for Rental, Infor.com (2013).

Waltermire et al, Applying the Continuous Monitoring Technical Reference Model to the Asset, Configuration, and Vulnerability Management Domains (DRAFT), NIST (Jan. 2012).

International Search Report and Written Opinion for Application No. PCT/US2018/033246, dated Oct. 5, 2018, 15 pages.

Intellectial Property Office of Singapore , Written Opinion dated Dec. 20, 2018, issued in connection with Singapore Application No. 11201710283S, filed on Dec. 11, 2017, 6 pages.

European Patent Office Extended Search Report for EP Application No. 16812206.7 dated Feb. 15, 2019, 7 pages.

European Patent Office Extended Search Report for EP Application No. 16812595.3 dated Jan. 11, 2019, 5 pages.

* cited by examiner

AGGREGATE PREDICTIVE MODEL AND WORKFLOW FOR LOCAL EXECUTION

CROSS REFERENCE TO RELATED APPLICATIONS

This application incorporates by reference U.S. Non-Provisional patent application Ser. No. 14/732,258, filed on Jun. 5, 2015, entitled Asset Health Score in its entirety. This application is also related to the following applications filed on the same day as the present application, each of which is incorporated by reference in its entirety: U.S. Non-Provisional patent application Ser. No. 14/744,362, entitled Dynamic Execution of Predictive Models & Workflows; and U.S. Non-Provisional patent application Ser. No. 14/744,369, entitled Individualized Predictive Model & Workflow for an Asset.

BACKGROUND

Today, machines (also referred to herein as "assets") are ubiquitous in many industries. From locomotives that transfer cargo across countries to medical equipment that helps nurses and doctors to save lives, assets serve an important role in everyday life. Depending on the role that an asset serves, its complexity, and cost, may vary. For instance, some assets may include multiple subsystems that must operate in harmony for the asset to function properly (e.g., an engine, transmission, etc. of a locomotive).

Because of the key role that assets play in everyday life, it is desirable for assets to be repairable with limited downtime. Accordingly, some have developed mechanisms to monitor and detect abnormal conditions within an asset to facilitate repairing the asset, perhaps with minimal downtime.

OVERVIEW

The current approach for monitoring assets generally involves an on-asset computer that receives signals from various sensors and/or actuators distributed throughout an asset that monitor the operating conditions of the asset. As one representative example, if the asset is a locomotive, the sensors and/or actuators may monitor parameters such as temperatures, voltages, and speeds, among other examples. If sensor and/or actuator signals from one or more of these devices reach certain values, the on-asset computer may then generate an abnormal-condition indicator, such as a "fault code," which is an indication that an abnormal condition has occurred within the asset.

In general, an abnormal condition may be a defect at an asset or component thereof, which may lead to a failure of the asset and/or component. As such, an abnormal condition may be associated with a given failure, or perhaps multiple failures, in that the abnormal condition is symptomatic of the given failure or failures. In practice, a user typically defines the sensors and respective sensor values associated with each abnormal-condition indicator. That is, the user defines an asset's "normal" operating conditions (e.g., those that do not trigger fault codes) and "abnormal" operating conditions (e.g., those that trigger fault codes).

After the on-asset computer generates an abnormal-condition indicator, the indicator and/or sensor signals may be passed to a remote location where a user may receive some indication of the abnormal condition and/or sensor signals and decide whether to take action. One action that the user might take is to assign a mechanic or the like to evaluate and potentially repair the asset. Once at the asset, the mechanic may connect a computing device to the asset and operate the computing device to cause the asset to utilize one or more local diagnostic tools to facilitate diagnosing the cause of the generated indicator.

While current asset-monitoring systems are generally effective at triggering abnormal-condition indicators, such systems are typically reactionary. That is, by the time the asset-monitoring system triggers an indicator, a failure within the asset may have already occurred (or is about to occur), which may lead to costly downtime, among other disadvantages. Additionally, due to the simplistic nature of on-asset abnormality-detection mechanisms in such asset-monitoring systems, current asset-monitoring approaches tend to involve a remote computing system performing monitoring computations for an asset and then transmitting instructions to the asset if a problem is detected. This may be disadvantageous due to network latency and/or infeasible when the asset moves outside of coverage of a communication network. Further still, due to the nature of local diagnostic tools stored on assets, current diagnosis procedures tend to be inefficient and cumbersome because a mechanic is required to cause the asset to utilize such tools.

The example systems, devices, and methods disclosed herein seek to help address one or more of these issues. In example implementations, a network configuration may include a communication network that facilitates communications between assets and a remote computing system. In some cases, the communication network may facilitate secure communications between assets and the remote computing system (e.g., via encryption or other security measures).

As noted above, each asset may include multiple sensors and/or actuators distributed throughout the asset that facilitate monitoring operating conditions of the asset. A number of assets may provide respective data indicative of each asset's operating conditions to the remote computing system, which may be configured to perform one or more operations based on the provided data. Typically, sensor and/or actuator data may be utilized for general asset-monitoring operations. However, as described herein, the remote computing system and/or assets may leverage such data to facilitate performing more complex operations.

In example implementations, the remote computing system may be configured to define and deploy to assets a predictive model and corresponding workflow (referred to herein as a "model-workflow pair") that are related to the operation of the assets. The assets may be configured to receive the model-workflow pair and utilize a local analytics device to operate in accordance with the model-workflow pair.

Generally, a model-workflow pair may cause an asset to monitor certain operating conditions and when certain conditions exist, modify a behavior that may help facilitate preventing an occurrence of a particular event. Specifically, a predictive model may receive as inputs sensor data from a particular set of asset sensors and output a likelihood that one or more particular events could occur at the asset within a particular period of time in the future. A workflow may involve one or more operations that are performed based on the likelihood of the one or more particular events that is output by the model.

In practice, the remote computing system may define an aggregate, predictive model and corresponding workflows, individualized, predictive models and corresponding workflows, or some combination thereof. An "aggregate" model/workflow may refer to a model/workflow that is generic for a group of assets, while an "individualized" model/workflow may refer to a model/workflow that is tailored for a single asset or subgroup of assets from the group of assts.

In example implementations, the remote computing system may start by defining an aggregate, predictive model based on historical data for multiple assets. Utilizing data for multiple assets may facilitate defining a more accurate predictive model than utilizing operating data for a single asset.

The historical data that forms the basis of the aggregate model may include at least operating data that indicates operating conditions of a given asset. Specifically, operating data may include abnormal-condition data identifying instances when failures occurred at assets and/or sensor data indicating one or more physical properties measured at the assets at the time of those instances. The data may also include environment data indicating environments in which assets have been operated and scheduling data indicating dates and times when assets were utilized, among other examples of asset-related data used to define the aggregate model-workflow pair.

Based on the historical data, the remote computing system may define an aggregate model that predicts the occurrence of particular events. In a particular example implementation, an aggregate model may output a probability that a failure will occur at an asset within a particular period of time in the future. Such a model may be referred to herein as a "failure model." Other aggregate models may predict the likelihood that an asset will complete a task within a particular period of time in the future, among other example predictive models.

After defining the aggregate model, the remote computing system may then define an aggregate workflow that corresponds to the defined aggregate model. Generally, a workflow may include one or more operations that an asset may perform based on a corresponding model. That is, the output of the corresponding model may cause the asset to perform workflow operations. For instance, an aggregate model-workflow pair may be defined such that when the aggregate model outputs a probability within a particular range an asset will execute a particular workflow operation, such as a local diagnostic tool.

After the aggregate model-workflow pair is defined, the remote computing system may transmit the pair to one or more assets. The one or more assets may then operate in accordance with the aggregate model-workflow pair.

In example implementations, the remote computing system may be configured to further define an individualized predictive model and/or corresponding workflow for one or multiple assets. The remote computing system may do so based on certain characteristics of each given asset, among other considerations. In example implementations, the remote computing system may start with an aggregate model-workflow pair as a baseline and individualize one or both of the aggregate model and workflow for the given asset based on the asset's characteristics.

In practice, the remote computing system may be configured to determine asset characteristics that are related to the aggregate model-workflow pair (e.g., characteristics of interest). Examples of such characteristics may include asset age, asset usage, asset class (e.g., brand and/or model), asset health, and environment in which an asset is operated, among other characteristics.

Then, the remote computing system may determine characteristics of the given asset that correspond to the characteristics of interest. Based at least on some of the given asset's characteristics, the remote computing system may be configured to individualize the aggregate model and/or corresponding workflow.

Defining an individualized model and/or workflow may involve the remote computing system making certain modifications to the aggregate model and/or workflow. For example, individualizing the aggregate model may involve changing model inputs, changing a model calculation, and/or changing a weight of a variable or output of a calculation, among other examples. Individualizing the aggregate workflow may involve changing one or more operations of the workflow and/or changing the model output value or range of values that triggers the workflow, among other examples.

After defining an individualized model and/or workflow for the given asset, the remote computing system may then transmit the individualized model and/or workflow to the given asset. In a scenario where only one of the model or workflow is individualized, the given asset may utilize the aggregate version of the model or workflow that is not individualized. The given asset may then operate in accordance with its individualized model-workflow pair.

In example implementations, a given asset may include a local analytics device that may be configured to cause the given asset to operate in accordance with a model-workflow pair provided by the remote computing system. The local analytics device may be configured to utilize operating data generated by the asset sensors and/or actuators (e.g., data that is typically utilized for other asset-related purposes) to run the predictive model. When the local analytics device receives certain operating data, it may execute the model and depending on the output of the model, may execute the corresponding workflow.

Executing the corresponding workflow may help facilitate preventing an undesirable event from occurring at the given asset. In this way, the given asset may locally determine that an occurrence of a particular event is likely and may then execute a particular workflow to help prevent the occurrence of the event. This may be particularly useful if communication between the given asset and remote computing system is hindered. For example, in some situations, a failure might occur before a command to take preventative actions reaches the given asset from the remote computing system. In such situations, the local analytics device may be advantageous in that it may generate the command locally, thereby avoiding any network latency or any issues arising from the given asset being "off-line." As such, the local analytics device executing a model-workflow pair may facilitate causing the asset to adapt to its conditions.

While a given asset is operating in accordance with a model-workflow pair, the given asset may also continue to provide operating data to the remote computing system. Based at least on this data, the remote computing system may modify the aggregate model-workflow pair and/or one or more individualized model-workflow pairs. The remote computing system may make modifications for a number of reasons.

In one example, the remote computing system may modify a model and/or workflow if a new event occurred at an asset that the model did not previously account for. For instance, in a failure model, the new event may be a new failure that had yet to occur at any of the assets whose data was used to define the aggregate model.

In another example, the remote computing system may modify a model and/or workflow if an event occurred at an asset under operating conditions that typically do not cause the event to occur. For instance, returning again to a failure model, the failure model or corresponding workflow may be modified if a failure occurred under operating conditions that had yet to cause the failure to occur in the past.

In yet another example, the remote computing system may modify a model and/or workflow if an executed workflow failed to prevent an occurrence of an event. Specifically, the remote computing system may modify the model and/or workflow if the output of the model caused an asset to execute a workflow aimed to prevent the occurrence of an event but the event occurred at the asset nonetheless. Other examples of reasons for modifying a model and/or workflow are also possible.

The remote computing system may then distribute any modifications to the asset whose data caused the modification and/or to other assets in communication with the remote computing system. In this way, the remote computing system may dynamically modify models and/or workflows and distribute these modifications to a whole fleet of assets based on operating conditions of an individual asset.

In some example implementations, an asset and/or the remote computing system may be configured to dynamically adjust executing a predictive model and/or workflow. In particular, the asset and/or remote computing system may be configured to detect certain events that trigger a change in responsibilities with respect to whether the asset and/or the remote computing system are executing a predictive model and/or workflow.

For instance, in some cases, after the asset receives a model-workflow pair from the remote computing system, the asset may store the model-workflow pair in data storage but then may rely on the remote computing system to centrally execute part or all of the model-workflow pair. On the other hand, in other cases, the remote computing system may rely on the asset to locally execute part or all of the model-workflow pair. In yet other cases, the remote computing system and the asset may share in the responsibilities of executing the model-workflow pair.

In any event, at some point in time, certain events may occur that trigger the asset and/or remote computing system to adjust the execution of the predictive model and/or workflow. For instance, the asset and/or remote computing system may detect certain characteristics of a communication network that couples the asset to the remote computing system. Based on the characteristics of the communication network, the asset may adjust whether it is locally executing a predictive model and/or workflow and the remote computing system may accordingly modify whether it is centrally executing the model and/or workflow. In this way, the asset and/or remote computing system may adapt to conditions of the asset.

In a particular example, the asset may detect an indication that a signal strength of a communication link between the asset and the remote computing system is relatively weak (e.g., the asset may determine that is about to go "off-line"), that a network latency is relatively high, and/or that a network bandwidth is relatively low. Accordingly, the asset may be programmed to take on responsibilities for executing the model-workflow pair that were previously being handled by the remote computing system. In turn, the remote computing system may cease centrally executing some or all of the model-workflow pair. In this way, the asset may locally execute the predictive model and then, based on executing the predictive model, execute the corresponding workflow to potentially help prevent an occurrence of a failure at the asset.

Moreover, in some implementations, the asset and/or the remote computing system may similarly adjust executing (or perhaps modify) a predictive model and/or workflow based on various other considerations. For example, based on the processing capacity of the asset, the asset may adjust locally executing a model-workflow pair and the remote computing system may accordingly adjust as well. In another example, based on the bandwidth of the communication network coupling the asset to the remote computing system, the asset may execute a modified workflow (e.g., transmitting data to the remote computing system according to a data-transmission scheme with a reduced transmission rate). Other examples are also possible.

As discussed above, examples provided herein are related to deployment and execution of predictive models. In one aspect, a computing system is provided. The computing system comprises at least one processor, a non-transitory computer-readable medium, and program instructions stored on the non-transitory computer-readable medium that are executable by the at least one processor to cause the computing system to: (a) receive respective operating data for a plurality of assets, (b) based on the received operating data, define a predictive model and a corresponding workflow that are related to the operation of the plurality of assets, and (c) transmit to at least one asset of the plurality of assets the predictive model and the corresponding workflow for local execution by the at least one asset.

In another aspect, a non-transitory computer-readable medium is provided having instructions stored thereon that are executable to cause a computing system to: (a) receive respective operating data for a plurality of assets, (b) based on the received operating data, define a predictive model and a corresponding workflow that are related to the operation of the plurality of assets, and (c) transmit to at least one asset of the plurality of assets the predictive model and the corresponding workflow for local execution by the at least one asset.

In yet another aspect, a computer-implemented method is provided. The method comprises: (a) receiving respective operating data for a plurality of assets, (b) based on the received operating data, defining a predictive model and a corresponding workflow that are related to the operation of the plurality of assets, and (c) transmitting to at least one asset of the plurality of assets the predictive model and the corresponding workflow for local execution by the at least one asset.

One of ordinary skill in the art will appreciate these as well as numerous other aspects in reading the following disclosure.

DETAILED DESCRIPTION

The following disclosure makes reference to the accompanying figures and several exemplary scenarios. One of ordinary skill in the art will understand that such references are for the purpose of explanation only and are therefore not meant to be limiting. Part or all of the disclosed systems, devices, and methods may be rearranged, combined, added to, and/or removed in a variety of manners, each of which is contemplated herein.

I. Example Network Configuration

Figure 1:
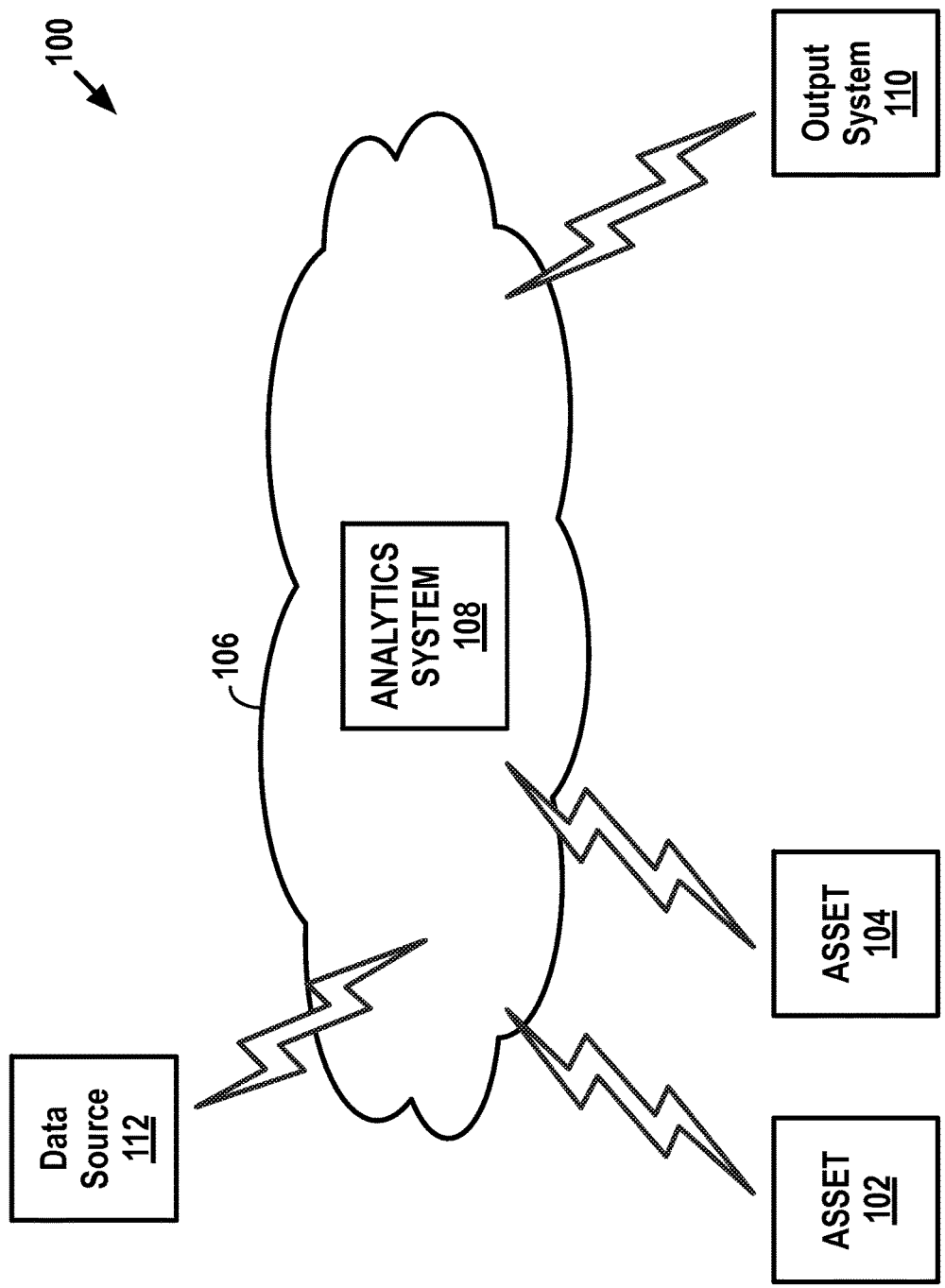
FIG. 1 depicts an example network configuration in which example embodiments may be implemented.

Turning now to the figures, FIG. 1 depicts an example network configuration 100 in which example embodiments may be implemented. As shown, the network configuration 100 includes an asset 102, an asset 104, a communication network 106, a remote computing system 108 that may take the form of an analytics system, an output system 110, and a data source 112.

The communication network 106 may communicatively connect each of the components in the network configuration 100. For instance, the assets 102 and 104 may communicate with the analytics system 108 via the communication network 106. In some cases, the assets 102 and 104 may communicate with one or more intermediary systems, such as an asset gateway (not pictured), that in turn communicates with the analytics system 108. Likewise, the analytics system 108 may communicate with the output system 110 via the communication network 106. In some cases, the analytics system 108 may communicate with one or more intermediary systems, such as a host server (not pictured), that in turn communicates with the output system 110. Many other configurations are also possible. In example cases, the communication network 106 may facilitate secure communications between network components (e.g., via encryption or other security measures).

In general, the assets 102 and 104 may take the form of any device configured to perform one or more operations (which may be defined based on the field) and may also include equipment configured to transmit data indicative of one or more operating conditions of the given asset. In some examples, an asset may include one or more subsystems configured to perform one or more respective operations. In practice, multiple subsystems may operate in parallel or sequentially in order for an asset to operate.

Example assets may include transportation machines (e.g., locomotives, aircraft, passenger vehicles, semi-trailer trucks, ships, etc.), industrial machines (e.g., mining equipment, construction equipment, factory automation, etc.), medical machines (e.g., medical imaging equipment, surgical equipment, medical monitoring systems, medical laboratory equipment, etc.), and utility machines (e.g., turbines, solar farms, etc.), among other examples. Those of ordinary skill in the art will appreciate that these are but a few examples of assets and that numerous others are possible and contemplated herein.

In example implementations, the assets 102 and 104 may each be of the same type (e.g., a fleet of locomotives or aircrafts, a group of wind turbines, or a set of MRI machines, among other examples) and perhaps may be of the same class (e.g., same brand and/or model). In other examples, the assets 102 and 104 may differ by type, by brand, by model, etc. The assets are discussed in further detail below with reference to FIG. 2.

As shown, the assets 102 and 104, and perhaps the data source 112, may communicate with the analytics system 108 via the communication network 106. In general, the communication network 106 may include one or more computing systems and network infrastructure configured to facilitate transferring data between network components. The communication network 106 may be or may include one or more Wide-Area Networks (WANs) and/or Local-Area Networks (LANs), which may be wired and/or wireless and support secure communication. In some examples, the communication network 106 may include one or more cellular networks and/or the Internet, among other networks. The communication network 106 may operate according to one or more communication protocols, such as LTE, CDMA, GSM, LPWAN, WiFi, Bluetooth, Ethernet, HTTP/S, TCP, CoAP/DTLS and the like. Although the communication network 106 is shown as a single network, it should be understood that the communication network 106 may include multiple, distinct networks that are themselves communicatively linked. The communication network 106 could take other forms as well.

As noted above, the analytics system 108 may be configured to receive data from the assets 102 and 104 and the data source 112. Broadly speaking, the analytics system 108 may include one or more computing systems, such as servers and databases, configured to receive, process, analyze, and output data. The analytics system 108 may be configured according to a given dataflow technology, such as TPL Dataflow or NiFi, among other examples. The analytics system 108 is discussed in further detail below with reference to FIG. 3.

As shown, the analytics system 108 may be configured to transmit data to the assets 102 and 104 and/or to the output system 110. The particular data transmitted may take various forms and will be described in further detail below.

In general, the output system 110 may take the form of a computing system or device configured to receive data and provide some form of output. The output system 110 may take various forms. In one example, the output system 110 may be or include an output device configured to receive data and provide an audible, visual, and/or tactile output in response to the data. In general, an output device may include one or more input interfaces configured to receive user input, and the output device may be configured to transmit data through the communication network 106 based on such user input. Examples of output devices include tablets, smartphones, laptop computers, other mobile computing devices, desktop computers, smart TVs, and the like.

Another example of the output system 110 may take the form of a work-order system configured to output a request for a mechanic or the like to repair an asset. Yet another example of the output system 110 may take the form of a parts-ordering system configured to place an order for a part of an asset and output a receipt thereof. Numerous other output systems are also possible.

The data source 112 may be configured to communicate with the analytics system 108. In general, the data source 112 may be or include one or more computing systems configured to collect, store, and/or provide to other systems, such as the analytics system 108, data that may be relevant to the functions performed by the analytics system 108. The data source 112 may be configured to generate and/or obtain data independently from the assets 102 and 104. As such, the data provided by the data source 112 may be referred to herein as "external data." The data source 112 may be configured to provide current and/or historical data. In practice, the analytics system 108 may receive data from the data source 112 by "subscribing" to a service provided by the data source. However, the analytics system 108 may receive data from the data source 112 in other manners as well.

Examples of the data source 112 include environment data sources, asset-management data sources, and other data sources. In general, environment data sources provide data indicating some characteristic of the environment in which assets are operated. Examples of environment data sources include weather-data servers, global navigation satellite systems (GNSS) servers, map-data servers, and topography-data servers that provide information regarding natural and artificial features of a given area, among other examples.

In general, asset-management data sources provide data indicating events or statuses of entities (e.g., other assets) that may affect the operation or maintenance of assets (e.g., when and where an asset may operate or receive maintenance). Examples of asset-management data sources include traffic-data servers that provide information regarding air, water, and/or ground traffic, asset-schedule servers that provide information regarding expected routes and/or locations of assets on particular dates and/or at particular times, defect detector systems (also known as "hotbox" detectors) that provide information regarding one or more operating conditions of an asset that passes in proximity to the defect detector system, part-supplier servers that provide information regarding parts that particular suppliers have in stock and prices thereof, and repair-shop servers that provide information regarding repair shop capacity and the like, among other examples.

Examples of other data sources include power-grid servers that provide information regarding electricity consumption and external databases that store historical operating data for assets, among other examples. One of ordinary skill in the art will appreciate that these are but a few examples of data sources and that numerous others are possible.

It should be understood that the network configuration 100 is one example of a network in which embodiments described herein may be implemented. Numerous other arrangements are possible and contemplated herein. For instance, other network configurations may include additional components not pictured and/or more or less of the pictured components.

II. Example Asset

Figure 2:
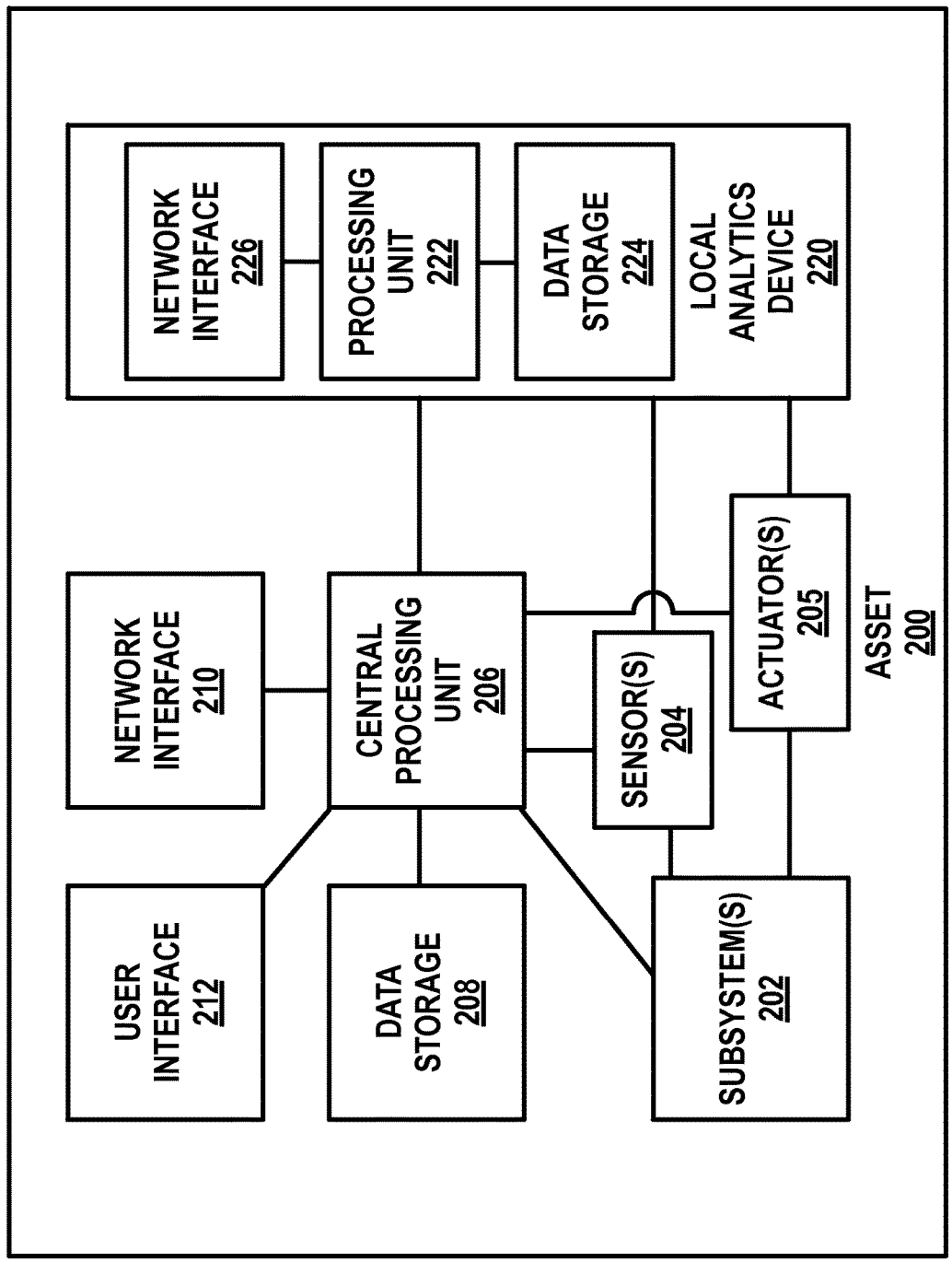
FIG. 2 depicts a simplified block diagram of an example asset.

Turning to FIG. 2, a simplified block diagram of an example asset 200 is depicted. Either or both of assets 102 and 104 from FIG. 1 may be configured like the asset 200. As shown, the asset 200 may include one or more subsystems 202, one or more sensors 204, one or more actuators 205, a central processing unit 206, data storage 208, a network interface 210, a user interface 212, and a local analytics device 220, all of which may be communicatively linked by a system bus, network, or other connection mechanism. One of ordinary skill in the art will appreciate that the asset 200 may include additional components not shown and/or more or less of the depicted components.

Broadly speaking, the asset 200 may include one or more electrical, mechanical, and/or electromechanical components configured to perform one or more operations. In some cases, one or more components may be grouped into a given subsystem 202.

Generally, a subsystem 202 may include a group of related components that are part of the asset 200. A single subsystem 202 may independently perform one or more operations or the single subsystem 202 may operate along with one or more other subsystems to perform one or more operations. Typically, different types of assets, and even different classes of the same type of assets, may include different subsystems.

For instance, in the context of transportation assets, examples of subsystems 202 may include engines, transmissions, drivetrains, fuel systems, battery systems, exhaust systems, braking systems, electrical systems, signal processing systems, generators, gear boxes, rotors, and hydraulic systems, among numerous other subsystems. In the context of a medical machine, examples of subsystems 202 may include scanning systems, motors, coil and/or magnet systems, signal processing systems, rotors, and electrical systems, among numerous other subsystems.

As suggested above, the asset 200 may be outfitted with various sensors 204 that are configured to monitor operating conditions of the asset 200 and various actuators 205 that are configured to interact with the asset 200 or a component thereof and monitor operating conditions of the asset 200. In some cases, some of the sensors 204 and/or actuators 205 may be grouped based on a particular subsystem 202. In this way, the group of sensors 204 and/or actuators 205 may be configured to monitor operating conditions of the particular subsystem 202, and the actuators from that group may be configured to interact with the particular subsystem 202 in some way that may alter the subsystem's behavior based on those operating conditions.

In general, a sensor 204 may be configured to detect a physical property, which may be indicative of one or more operating conditions of the asset 200, and provide an indication, such as an electrical signal, of the detected physical property. In operation, the sensors 204 may be configured to obtain measurements continuously, periodically (e.g., based on a sampling frequency), and/or in response to some triggering event. In some examples, the sensors 204 may be preconfigured with operating parameters for performing measurements and/or may perform measurements in accordance with operating parameters provided by the central processing unit 206 (e.g., sampling signals that instruct the sensors 204 to obtain measurements). In examples, different sensors 204 may have different operating parameters (e.g., some sensors may sample based on a first frequency, while other sensors sample based on a second, different frequency). In any event, the sensors 204 may be configured to transmit electrical signals indicative of a measured physical property to the central processing unit 206. The sensors 204 may continuously or periodically provide such signals to the central processing unit 206.

For instance, sensors 204 may be configured to measure physical properties such as the location and/or movement of the asset 200, in which case the sensors may take the form of GNSS sensors, dead-reckoning-based sensors, accelerometers, gyroscopes, pedometers, magnetometers, or the like.

Additionally, various sensors 204 may be configured to measure other operating conditions of the asset 200, examples of which may include temperatures, pressures, speeds, acceleration or deceleration rates, friction, power usages, fuel usages, fluid levels, runtimes, voltages and currents, magnetic fields, electric fields, presence or absence of objects, positions of components, and power generation, among other examples. One of ordinary skill in the art will appreciate that these are but a few example operating conditions that sensors may be configured to measure. Additional or fewer sensors may be used depending on the industrial application or specific asset.

As suggested above, an actuator 205 may be configured similar in some respects to a sensor 204. Specifically, an actuator 205 may be configured to detect a physical property indicative of an operating condition of the asset 200 and provide an indication thereof in a manner similar to the sensor 204.

Moreover, an actuator 205 may be configured to interact with the asset 200, one or more subsystems 202, and/or some component thereof. As such, an actuator 205 may include a motor or the like that is configured to move or otherwise control a component or system. In a particular example, an actuator may be configured to measure a fuel flow and alter the fuel flow (e.g., restrict the fuel flow), or an actuator may be configured to measure a hydraulic pressure and alter the hydraulic pressure (e.g., increase or decrease the hydraulic pressure). Numerous other example interactions of an actuator are also possible and contemplated herein.

Generally, the central processing unit 206 may include one or more processors and/or controllers, which may take the form of a general- or special-purpose processor or controller. In particular, in example implementations, the central processing unit 206 may be or include microprocessors, microcontrollers, application specific integrated circuits, digital signal processors, and the like. In turn, the data storage 208 may be or include one or more non-transitory computer-readable storage media, such as optical, magnetic, organic, or flash memory, among other examples.

The central processing unit 206 may be configured to store, access, and execute computer-readable program instructions stored in the data storage 208 to perform the operations of an asset described herein. For instance, as suggested above, the central processing unit 206 may be configured to receive respective sensor signals from the sensors 204 and/or actuators 205. The central processing unit 206 may be configured to store sensor and/or actuator data in and later access it from the data storage 208.

The central processing unit 206 may also be configured to determine whether received sensor and/or actuator signals trigger any abnormal-condition indicators, such as fault codes. For instance, the central processing unit 206 may be configured to store in the data storage 208 abnormal-condition rules, each of which include a given abnormal-condition indicator representing a particular abnormal condition and respective triggering criteria that trigger the abnormal-condition indicator. That is, each abnormal-condition indicator corresponds with one or more sensor and/or actuator measurement values that must be satisfied before the abnormal-condition indicator is triggered. In practice, the asset 200 may be pre-programmed with the abnormal-condition rules and/or may receive new abnormal-condition rules or updates to existing rules from a computing system, such as the analytics system 108.

In any event, the central processing unit 206 may be configured to determine whether received sensor and/or actuator signals trigger any abnormal-condition indicators. That is, the central processing unit 206 may determine whether received sensor and/or actuator signals satisfy any triggering criteria. When such a determination is affirmative, the central processing unit 206 may generate abnormal-condition data and may also cause the asset's user interface 212 to output an indication of the abnormal condition, such as a visual and/or audible alert. Additionally, the central processing unit 206 may log the occurrence of the abnormal-condition indicator being triggered in the data storage 208, perhaps with a timestamp.

Figure 3:
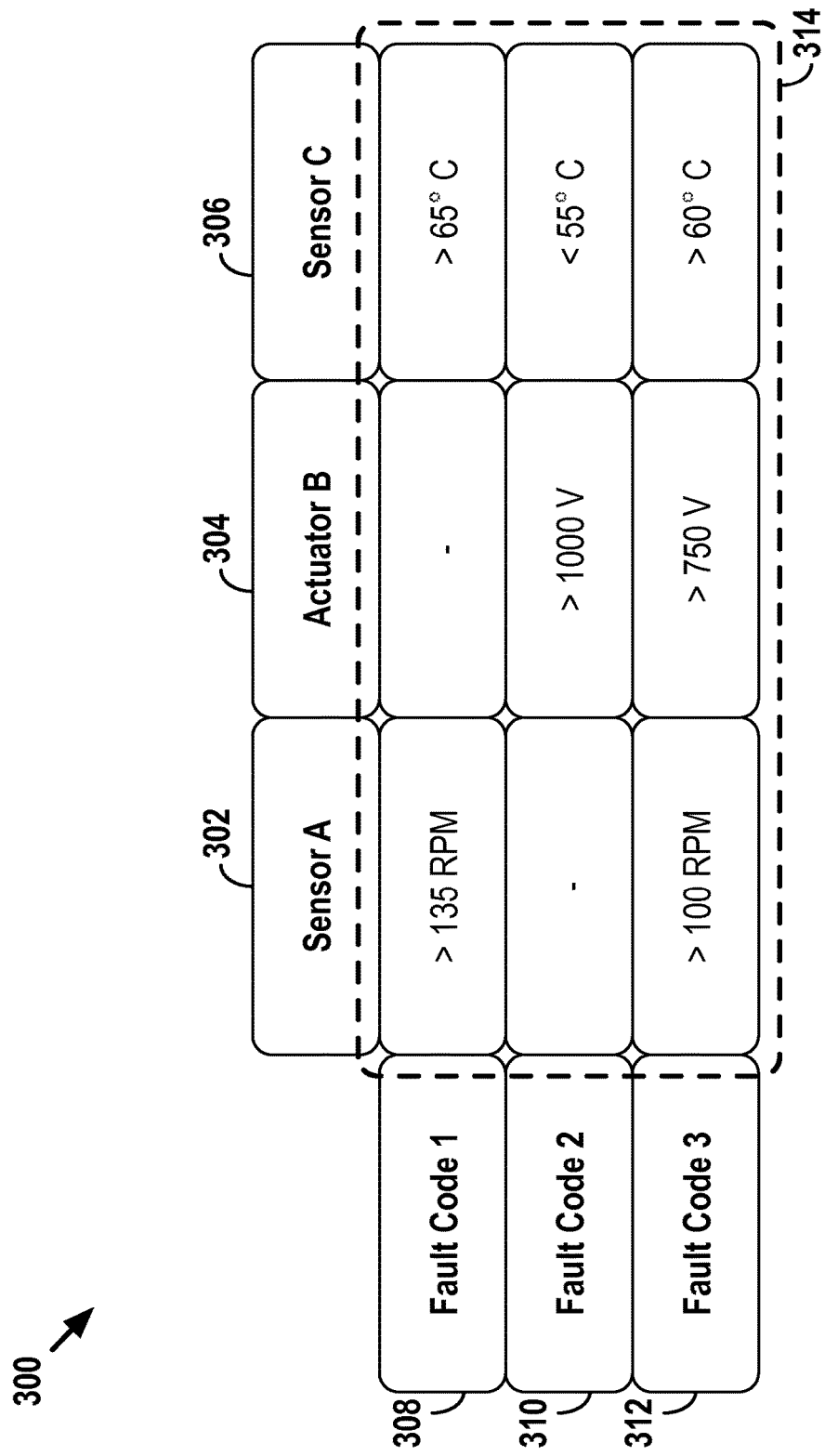
FIG. 3 depicts a conceptual illustration of example abnormal-condition indicators and triggering criteria.

FIG. 3 depicts a conceptual illustration of example abnormal-condition indicators and respective triggering criteria for an asset. In particular, FIG. 3 depicts a conceptual illustration of example fault codes. As shown, table 300 includes columns 302, 304, and 306 that correspond to Sensor A, Actuator B, and Sensor C, respectively, and rows 308, 310, and 312 that correspond to Fault Codes 1, 2, and 3, respectively. Entries 314 then specify sensor criteria (e.g., sensor value thresholds) that correspond to the given fault codes.

For example, Fault Code 1 will be triggered when Sensor A detects a rotational measurement greater than 135 revolutions per minute (RPM) and Sensor C detects a temperature measurement greater than 65° Celsius (C), Fault Code 2 will be triggered when Actuator B detects a voltage measurement greater than 1000 Volts (V) and Sensor C detects a temperature measurement less than 55° C., and Fault Code 3 will be triggered when Sensor A detects a rotational measurement greater than 100 RPM, Actuator B detects a voltage measurement greater than 750 V, and Sensor C detects a temperature measurement greater than 60° C. One of ordinary skill in the art will appreciate that FIG. 3 is provided for purposes of example and explanation only and that numerous other fault codes and/or triggering criteria are possible and contemplated herein.

Referring back to FIG. 2, the central processing unit 206 may be configured to carry out various additional functions for managing and/or controlling operations of the asset 200 as well. For example, the central processing unit 206 may be configured to provide instruction signals to the subsystems 202 and/or the actuators 205 that cause the subsystems 202 and/or the actuators 205 to perform some operation, such as modifying a throttle position. Additionally, the central processing unit 206 may be configured to modify the rate at which it processes data from the sensors 204 and/or the actuators 205, or the central processing unit 206 may be configured to provide instruction signals to the sensors 204 and/or actuators 205 that cause the sensors 204 and/or actuators 205 to, for example, modify a sampling rate. Moreover, the central processing unit 206 may be configured to receive signals from the subsystems 202, the sensors 204, the actuators 205, the network interfaces 210, and/or the user interfaces 212 and based on such signals, cause an operation to occur. Further still, the central processing unit 206 may be configured to receive signals from a computing device, such as a diagnostic device, that cause the central processing unit 206 to execute one or more diagnostic tools in accordance with diagnostic rules stored in the data storage 208. Other functionalities of the central processing unit 206 are discussed below.

The network interface 210 may be configured to provide for communication between the asset 200 and various network components connected to communication network 106. For example, the network interface 210 may be configured to facilitate wireless communications to and from the communication network 106 and may thus take the form of an antenna structure and associated equipment for transmitting and receiving various over-the-air signals. Other examples are possible as well. In practice, the network interface 210 may be configured according to a communication protocol, such as but not limited to any of those described above.

The user interface 212 may be configured to facilitate user interaction with the asset 200 and may also be configured to facilitate causing the asset 200 to perform an operation in response to user interaction. Examples of user interfaces 212 include touch-sensitive interfaces, mechanical interfaces (e.g., levers, buttons, wheels, dials, keyboards, etc.), and other input interfaces (e.g., microphones), among other examples. In some cases, the user interface 212 may include or provide connectivity to output components, such as display screens, speakers, headphone jacks, and the like.

The local analytics device 220 may generally be configured to receive and analyze data and based on such analysis, cause one or more operations to occur at the asset 200. In particular, the local analytics device 220 may receive data from the sensors 204 and/or actuators 205 and based on such data, may provide instructions to the central processing unit 206 that cause the asset 200 to perform an operation.

In practice, the local analytics device 220 may enable the asset 200 to locally perform advanced analytics and associated operations, such as executing a predictive model and corresponding workflow, that may otherwise not be able to be performed with the other on-asset components. As such, the local analytics device 220 may help provide additional processing power and/or intelligence to the asset 200.

As shown, the local analytics device 220 may include a processing unit 222, a data storage 224, and a network interface 226, all of which may be communicatively linked by a system bus, network, or other connection mechanism. The processing unit 222 may include any of the components discussed above with respect to the central processing unit 206. In turn, the data storage 224 may be or include one or more non-transitory computer-readable storage media, which may take any of the forms of computer-readable storage media discussed above.

The processing unit 222 may be configured to store, access, and execute computer-readable program instructions stored in the data storage 224 to perform the operations of a local analytics device described herein. For instance, the processing unit 222 may be configured to receive respective sensor and/or actuator signals from the sensors 204 and/or actuators 205 and execute a predictive model-workflow pair based on such signals. Other functions are described below.

The network interface 226 may be the same or similar to the network interfaces described above. In practice, the network interface 226 may facilitate communication between the asset 200 and the analytics system 108.

In some example implementations, the local analytics device 220 may include and/or communicate with a user interface that may be similar to the user interface 212. In practice, the user interface may be located remotely from the local analytics device 220 (and the asset 200). Other examples are also possible.

One of ordinary skill in the art will appreciate that the asset 200 shown in FIG. 2 is but one example of a simplified representation of an asset and that numerous others are also possible. For instance, other assets may include additional components not pictured and/or more or less of the pictured components. Moreover, a given asset may include multiple, individual assets that are operated in concert to perform operations of the given asset. Other examples are also possible.

III. Example Analytics System

Figure 4:
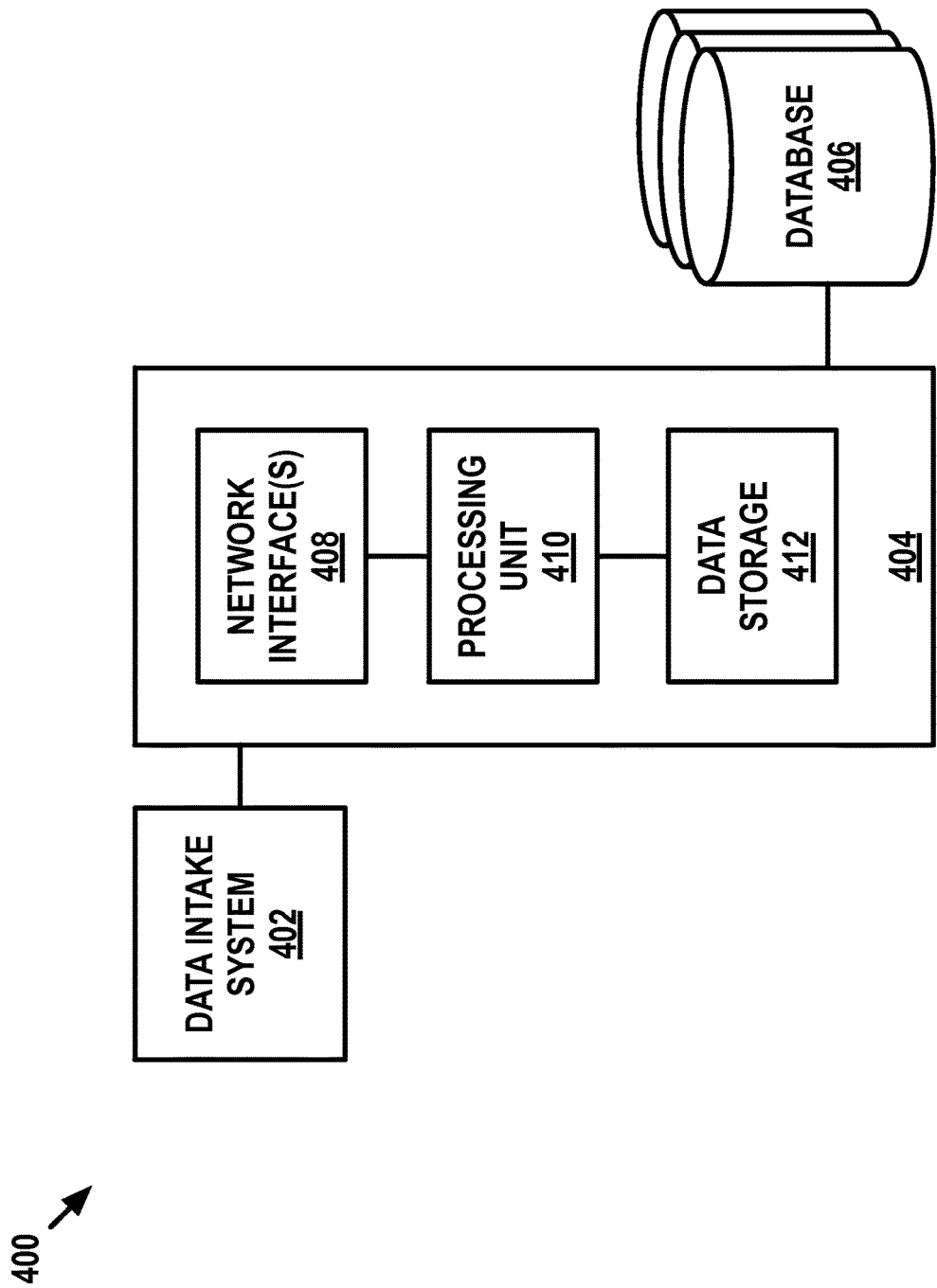
FIG. 4 depicts a simplified block diagram of an example analytics system.

Referring now to FIG. 4, a simplified block diagram of an example analytics system 400 is depicted. As suggested above, the analytics system 400 may include one or more computing systems communicatively linked and arranged to carry out various operations described herein. Specifically, as shown, the analytics system 400 may include a data intake system 402, a data science system 404, and one or more databases 406. These system components may be communicatively coupled via one or more wireless and/or wired connections, which may be configured to facilitate secure communications.

The data intake system 402 may generally function to receive and process data and output data to the data science system 404. As such, the data intake system 402 may include one or more network interfaces configured to receive data from various network components of the network configuration 100, such as the assets 102 and 104, the output system 110, and/or the data source 112. Specifically, the data intake system 402 may be configured to receive analog signals, data streams, and/or network packets, among other examples. As such, the network interfaces may include one or more wired network interfaces, such as a port or the like, and/or wireless network interfaces, similar to those described above. In some examples, the data intake system 402 may be or include components configured according to a given dataflow technology, such as a NiFi receiver or the like.

The data intake system 402 may include one or more processing components configured to perform one or more operations. Example operations may include compression and/or decompression, encryption and/or de-encryption, analog-to-digital and/or digital-to-analog conversion, filtration, and amplification, among other operations. Moreover, the data intake system 402 may be configured to parse, sort, organize, and/or route data based on data type and/or characteristics of the data. In some examples, the data intake system 402 may be configured to format, package, and/or route data based on one or more characteristics or operating parameters of the data science system 404.

In general, the data received by the data intake system 402 may take various forms. For example, the payload of the data may include a single sensor or actuator measurement, multiple sensor and/or actuator measurements and/or one or more abnormal-condition data. Other examples are also possible.

Moreover, the received data may include certain characteristics, such as a source identifier and a timestamp (e.g., a date and/or time at which the information was obtained). For instance, a unique identifier (e.g., a computer generated alphabetic, numeric, alphanumeric, or the like identifier) may be assigned to each asset, and perhaps to each sensor and actuator. Such identifiers may be operable to identify the asset, sensor, or actuator from which data originates. In some cases, another characteristic may include the location (e.g., GPS coordinates) at which the information was obtained. Data characteristics may come in the form of signal signatures or metadata, among other examples.

The data science system 404 may generally function to receive (e.g., from the data intake system 402) and analyze data and based on such analysis, cause one or more operations to occur. As such, the data science system 404 may include one or more network interfaces 408, a processing unit 410, and data storage 412, all of which may be communicatively linked by a system bus, network, or other connection mechanism. In some cases, the data science system 404 may be configured to store and/or access one or more application program interfaces (APIs) that facilitate carrying out some of the functionality disclosed herein.

The network interfaces 408 may be the same or similar to any network interface described above. In practice, the network interfaces 408 may facilitate communication (e.g., with some level of security) between the data science system 404 and various other entities, such as the data intake system 402, the databases 406, the assets 102, the output system 110, etc.

The processing unit 410 may include one or more processors, which may take any of the processor forms described above. In turn, the data storage 412 may be or include one or more non-transitory computer-readable storage media, which may take any of the forms of computer-readable storage media discussed above. The processing unit 410 may be configured to store, access, and execute computer-readable program instructions stored in the data storage 412 to perform the operations of an analytics system described herein.

In general, the processing unit 410 may be configured to perform analytics on data received from the data intake system 402. To that end, the processing unit 410 may be configured to execute one or more modules, which may each take the form of one or more sets of program instructions that are stored in the data storage 412. The modules may be configured to facilitate causing an outcome to occur based on the execution of the respective program instructions. An example outcome from a given module may include outputting data into another module, updating the program instructions of the given module and/or of another module, and outputting data to a network interface 408 for transmission to an asset and/or the output system 110, among other examples.

The databases 406 may generally function to receive (e.g., from the data science system 404) and store data. As such, each database 406 may include one or more non-transitory computer-readable storage media, such as any of the examples provided above. In practice, the databases 406 may be separate from or integrated with the data storage 412.

The databases 406 may be configured to store numerous types of data, some of which is discussed below. In practice, some of the data stored in the databases 406 may include a timestamp indicating a date and time at which the data was generated or added to the database. Moreover, data may be stored in a number of manners in the databases 406. For instance, data may be stored in time sequence, in a tabular manner, and/or organized based on data source type (e.g., based on asset, asset type, sensor, sensor type, actuator, or actuator type) or abnormal-condition indicator, among other examples.

IV. Example Operations

The operations of the example network configuration 100 depicted in FIG. 1 will now be discussed in further detail below. To help describe some of these operations, flow diagrams may be referenced to describe combinations of operations that may be performed. In some cases, each block may represent a module or portion of program code that includes instructions that are executable by a processor to implement specific logical functions or steps in a process. The program code may be stored on any type of computer-readable medium, such as non-transitory computer-readable media. In other cases, each block may represent circuitry that is wired to perform specific logical functions or steps in a process. Moreover, the blocks shown in the flow diagrams may be rearranged into different orders, combined into fewer blocks, separated into additional blocks, and/or removed based upon the particular embodiment.

The following description may reference examples where a single data source, such as the asset 102, provides data to the analytics system 108 that then performs one or more functions. It should be understood that this is done merely for sake of clarity and explanation and is not meant to be limiting. In practice, the analytics system 108 generally receives data from multiple sources, perhaps simultaneously, and performs operations based on such aggregate received data.

A. Collection of Operating Data

As mentioned above, the representative asset 102 may take various forms and may be configured to perform a number of operations. In a non-limiting example, the asset 102 may take the form of a locomotive that is operable to transfer cargo across the United States. While in transit, the sensors and/or actuators of the asset 102 may obtain data that reflects one or more operating conditions of the asset 102. The sensors and/or actuators may transmit the data to a processing unit of the asset 102.

The processing unit may be configured to receive the data from the sensors and/or actuators. In practice, the processing unit may receive sensor data from multiple sensors and/or actuator data from multiple actuators simultaneously or sequentially. As discussed above, while receiving this data, the processing unit may also be configured to determine whether the data satisfies triggering criteria that trigger any abnormal-condition indicators, such as fault codes. In the event the processing unit determines that one or more abnormal-condition indicators are triggered, the processing unit may be configured to perform one or more local operations, such as outputting an indication of the triggered indicator via a user interface.

The asset 102 may then transmit operating data to the analytics system 108 via a network interface of the asset 102 and the communication network 106. In operation, the asset 102 may transmit operating data to the analytics system 108 continuously, periodically, and/or in response to triggering events (e.g., abnormal conditions). Specifically, the asset 102 may transmit operating data periodically based on a particular frequency (e.g., daily, hourly, every fifteen minutes, once per minute, once per second, etc.), or the asset 102 may be configured to transmit a continuous, real-time feed of operating data. Additionally or alternatively, the asset 102 may be configured to transmit operating data based on certain triggers, such as when sensor and/or actuator measurements satisfy triggering criteria for any abnormal-condition indicators. The asset 102 may transmit operating data in other manners as well.

In practice, operating data for the asset 102 may include sensor data, actuator data, and/or abnormal-condition data. In some implementations, the asset 102 may be configured to provide the operating data in a single data stream, while in other implementations the asset 102 may be configured to provide the operating data in multiple, distinct data streams. For example, the asset 102 may provide to the analytics system 108 a first data stream of sensor and/or actuator data and a second data stream of abnormal-condition data. Other possibilities also exist.

Sensor and actuator data may take various forms. For example, at times, sensor data (or actuator data) may include measurements obtained by each of the sensors (or actuators) of the asset 102. While at other times, sensor data (or actuator data) may include measurements obtained by a subset of the sensors (or actuators) of the asset 102.

Specifically, the sensor and/or actuator data may include measurements obtained by the sensors and/or actuators associated with a given triggered abnormal-condition indicator. For example, if a triggered fault code is Fault Code 1 from FIG. 3, then sensor data may include raw measurements obtained by Sensors A and C. Additionally or alternatively, the data may include measurements obtained by one or more sensors or actuators not directly associated with the triggered fault code. Continuing off the last example, the data may additionally include measurements obtained by Actuator B and/or other sensors or actuators. In some examples, the asset 102 may include particular sensor data in the operating data based on a fault-code rule or instruction provided by the analytics system 108, which may have, for example, determined that there is a correlation between that which Actuator B is measuring and that which caused the Fault Code 1 to be triggered in the first place. Other examples are also possible.

Further still, the data may include one or more sensor and/or actuator measurements from each sensor and/or actuator of interest based on a particular time of interest, which may be selected based on a number of factors. In some examples, the particular time of interest may be based on a sampling rate. In other examples, the particular time of interest may be based on the time at which an abnormal-condition indicator is triggered.

In particular, based on the time at which an abnormal-condition indicator is triggered, the data may include one or more respective sensor and/or actuator measurements from each sensor and/or actuator of interest (e.g., sensors and/or actuators directly and indirectly associated with the triggered indicator). The one or more measurements may be based on a particular number of measurements or particular duration of time around the time of the triggered abnormal-condition indicator.

For example, if a triggered fault code is Fault Code 2 from FIG. 3, the sensors and actuators of interest might include Actuator B and Sensor C. The one or more measurements may include the most recent respective measurements obtained by Actuator B and Sensor C prior to the triggering of the fault code (e.g., triggering measurements) or a respective set of measurements before, after, or about the triggering measurements. For example, a set of five measurements may include the five measurements before or after the triggering measurement (e.g., excluding the triggering measurement), the four measurements before or after the triggering measurement and the triggering measurement, or the two measurements before and the two after as well as the triggering measurement, among other possibilities.

Similar to sensor and actuator data, the abnormal-condition data may take various forms. In general, the abnormal-condition data may include or take the form of an indicator that is operable to uniquely identify a particular abnormal condition that occurred at the asset 102 from all other abnormal conditions that may occur at the asset 102. The abnormal-condition indicator may take the form of an alphabetic, numeric, or alphanumeric identifier, among other examples. Moreover, the abnormal-condition indicator may take the form of a string of words that is descriptive of the abnormal condition, such as "Overheated Engine" or "Out of Fuel", among other examples.

The analytics system 108, and in particular, the data intake system of the analytics system 108, may be configured to receive operating data from one or more assets and/or data sources. The data intake system may be configured to perform one or more operations to the received data and then relay the data to the data science system of the analytics system 108. In turn, the data science system may analyze the received data and based on such analysis, perform one or more operations.

B. Defining Predictive Models & Workflows

As one example, the analytics system 108 may be configured to define predictive models and corresponding workflows based on received operating data for one or more assets and/or received external data related to the one or more assets. The analytics system 108 may define model-workflow pairs based on various other data as well.

In general, a model-workflow pair may include a set of program instructions that cause an asset to monitor certain operating conditions and carry out certain operations that help facilitate preventing the occurrence of a particular event suggested by the monitored operating conditions. Specifically, a predictive model may include one or more algorithms whose inputs are sensor and/or actuator data from one or more sensors and/or actuators of an asset and whose outputs are utilized to determine a probability that a particular event may occur at the asset within a particular period of time in the future. In turn, a workflow may include one or more triggers (e.g., model output values) and corresponding operations that the asset carries out based on the triggers.

As suggested above, the analytics system 108 may be configured to define aggregate and/or individualized predictive models and/or workflows. An "aggregate" model/workflow may refer to a model/workflow that is generic for a group of assets and defined without taking into consideration particular characteristics of the assets to which the model/workflow is deployed. On the other hand, an "individualized" model/workflow may refer to a model/workflow that is specifically tailored for a single asset or a subgroup of assets from the group of assets and defined based on particular characteristics of the single asset or subgroup of assets to which the model/workflow is deployed. These different types of models/workflows and the operations performed by the analytics system 108 to define them are discussed in further detail below.

1. Aggregate Models & Workflows

In example implementations, the analytics system 108 may be configured to define an aggregate model-workflow pair based on aggregated data for a plurality of assets. Defining aggregate model-workflow pairs may be performed in a variety of manners.

Figure 5:
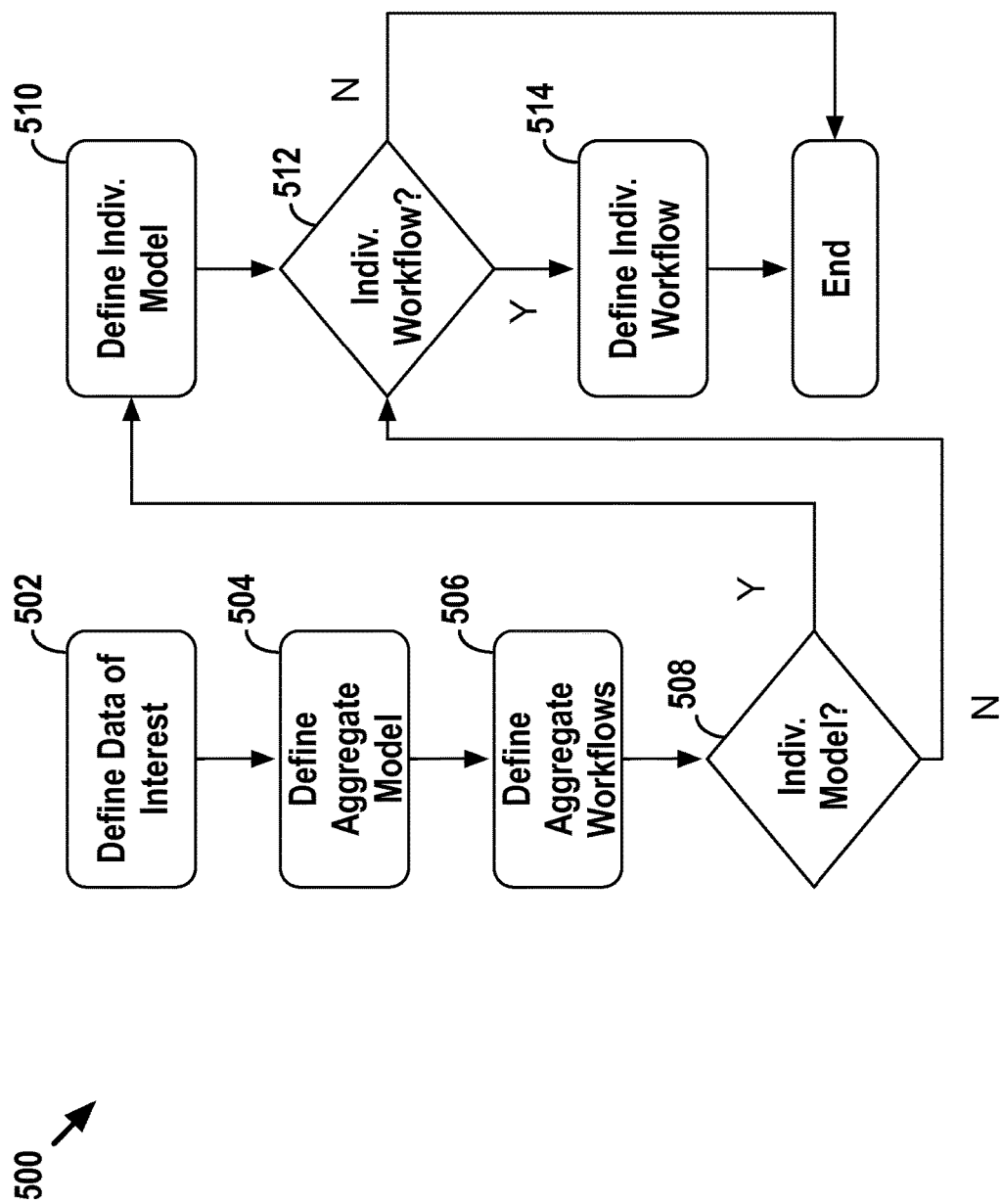
FIG. 5 depicts an example flow diagram of a definition phase that may be used for defining model-workflow pairs.

FIG. 5 is a flow diagram 500 depicting one possible example of a definition phase that may be used for defining model-workflow pairs. For purposes of illustration, the example definition phase is described as being carried out by the analytics system 108, but this definition phase may be carried out by other systems as well. One of ordinary skill in the art will appreciate that the flow diagram 500 is provided for sake of clarity and explanation and that numerous other combinations of operations may be utilized to define a model-workflow pair.

As shown in FIG. 5, at block 502, the analytics system 108 may begin by defining a set of data that forms the basis for a given predictive model (e.g., the data of interest). The data of interest may derive from a number of sources, such as the assets 102 and 104 and the data source 112, and may be stored in a database of the analytics system 108.

The data of interest may include historical data for a particular set of assets from a group of assets or all of the assets from a group of assets (e.g., the assets of interest).

Moreover, the data of interest may include measurements from a particular set of sensors and/or actuators from each of the assets of interest or from all of the sensors and/or actuators from each of the assets of interest. Further still, the data of interest may include data from a particular period of time in the past, such as two week's worth of historical data.

The data of interest may include a variety of types data, which may depend on the given predictive model. In some instances, the data of interest may include at least operating data indicating operating conditions of assets, where the operating data is as discussed above in the Collection of Operating Data section. Additionally, the data of interest may include environment data indicating environments in which assets are typically operated and/or scheduling data indicating planned dates and times during which assets are to carry out certain tasks. Other types of data may also be included in the data of interest.

In practice, the data of interest may be defined in a number of manners. In one example, the data of interest may be user-defined. In particular, a user may operate an output system 110 that receives user inputs indicating a selection of certain data of interest, and the output system 110 may provide to the analytics system 108 data indicating such selections. Based on the received data, the analytics system 108 may then define the data of interest.

In another example, the data of interest may be machine-defined. In particular, the analytics system 108 may perform various operations, such as simulations, to determine the data of interest that generates the most accurate predictive model. Other examples are also possible.

Returning to FIG. 5, at block 504, the analytics system 108 may be configured to, based on the data of interest, define an aggregate, predictive model that is related to the operation of assets. In general, an aggregate, predictive model may define a relationship between operating conditions of assets and a likelihood of an event occurring at the assets. Specifically, an aggregate, predictive model may receive as inputs sensor data from sensors of an asset and/or actuator data from actuators of the asset and output a probability that an event will occur at the asset within a certain amount of time into the future.

The event that the predictive model predicts may vary depending on the particular implementation. For example, the event may be a failure and so, the predictive model may be a failure model that predicts whether a failure will occur within a certain period of time in the future (failure models are discussed in detail below in the Health-Score Models & Workflows section). In another example, the event may be an asset completing a task and so, the predictive model may predict the likelihood that an asset will complete a task on time. In other examples, the event may be a fluid or component replacement, and so, the predictive model may predict an amount of time before a particular asset fluid or component needs to be replaced. In yet other examples, the event may be a change in asset productivity, and so, the predictive model may predict the productivity of an asset during a particular period of time in the future. In one other example, the event may be the occurrence of a "leading indicator" event, which may indicate an asset behavior that differs from expected asset behaviors, and so, the predictive model may predict the likelihood of one or more leading indicator events occurring in the future. Other examples of predictive models are also possible.

In any event, the analytics system 108 may define the aggregate, predictive model in a variety of manners. In general, this operation may involve utilizing one or more modeling techniques to generate a model that returns a probability between zero and one, such as a random forest technique, logistic regression technique, or other regression technique, among other modeling techniques. In a particular example implementation, the analytics system 108 may define the aggregate, predictive model in line with the below discussion referencing FIG. 7. The analytics system 108 may define the aggregate model in other manners as well.

At block 506, the analytics system 108 may be configured to define an aggregate workflow that corresponds to the defined model from block 504. In general, a workflow may take the form of an action that is carried out based on a particular output of a predictive model. In example implementations, a workflow may include one or more operations that an asset performs based on the output of the defined predictive model. Examples of operations that may be part of a workflow include an asset acquiring data according to a particular data-acquisition scheme, transmitting data to the analytics system 108 according to a particular data-transmission scheme, executing a local diagnostic tool, and/or modifying an operating condition of the asset, among other example workflow operations.

A particular data-acquisition scheme may indicate how an asset acquires data. In particular, a data-acquisition scheme may indicate certain sensors and/or actuators from which the asset obtains data, such as a subset of sensors and/or actuators of the asset's plurality of sensors and actuators (e.g., sensors/actuators of interest). Further, a data-acquisition scheme may indicate an amount of data that the asset obtains from the sensors/actuators of interest and/or a sampling frequency at which the asset acquires such data. Data-acquisition schemes may include various other attributes as well. In a particular example implementation, a particular data-acquisition scheme may correspond to a predictive model for asset health and may be adjusted to acquire more data and/or particular data (e.g., from particular sensors) based on a decreasing asset health. Or a particular data-acquisition scheme may correspond to a leading-indicators predictive model and may be adjusted to a modify data acquired by asset sensors and/or actuators based on an increased likelihood of an occurrence of a leading indicator event that may signal that a subsystem failure might occur.

A particular data-transmission scheme may indicate how an asset transmits data to the analytics system 108. Specifically, a data-transmission scheme may indicate a type of data (and may also indicate a format and/or structure of the data) that the asset should transmit, such as data from certain sensors or actuators, a number of data samples that the asset should transmit, a transmission frequency, and/or a priority-scheme for the data that the asset should include in its data transmission. In some cases, a particular data-acquisition scheme may include a data-transmission scheme or a data-acquisition scheme may be paired with a data-transmission scheme. In some example implementations, a particular data-transmission scheme may correspond to a predictive model for asset health and may be adjusted to transmit data less frequently based on an asset health that is above a threshold value. Other examples are also possible.

As suggested above, a local diagnostic tool may be a set of procedures or the like that are stored locally at an asset. The local diagnostic tool may generally facilitate diagnosing a cause of a fault or failure at an asset. In some cases, when executed, a local diagnostic tool may pass test inputs into a subsystem of an asset or a portion thereof to obtain test results, which may facilitate diagnosing the cause of a fault or failure. These local diagnostic tools are typically dormant on an asset and will not be executed unless the asset receives particular diagnostic instructions. Other local diagnostic tools are also possible. In one example implementation, a particular local diagnostic tool may correspond to a predictive model for health of a subsystem of an asset and may be executed based on a subsystem health that is at or below a threshold value.

Lastly, a workflow may involve modifying an operating condition of an asset. For instance, one or more actuators of an asset may be controlled to facilitate modifying an operating condition of the asset. Various operating conditions may be modified, such as a speed, temperature, pressure, fluid level, current draw, and power distribution, among other examples. In a particular example implementation, an operating-condition modification workflow may correspond to a predictive model for predicting whether an asset will complete a task on time and may cause the asset to increase its speed of travel based on a predicted completion percentage that is below a threshold value.

In any event, the aggregate workflow may be defined in a variety of manners. In one example, the aggregate workflow may be user defined. Specifically, a user may operate a computing device that receives user inputs indicating selection of certain workflow operations, and the computing device may provide to the analytics system 108 data indicating such selections. Based on this data, the analytics system 108 may then define the aggregate workflow.

In another example, the aggregate workflow may be machine-defined. In particular, the analytics system 108 may perform various operations, such as simulations, to determine a workflow that may facilitate determining a cause of the probability output by the predictive model and/or preventing an occurrence of an event predicted by the model. Other examples of defining the aggregate workflow are also possible.

In defining the workflow corresponding to the predictive model, the analytics system 108 may define the triggers of the workflow. In example implementations, a workflow trigger may be a value of the probability output by the predictive model or a range of values output by the predictive model. In some cases, a workflow may have multiple triggers, each of which may cause a different operation or operations to occur.

Figure 6A:
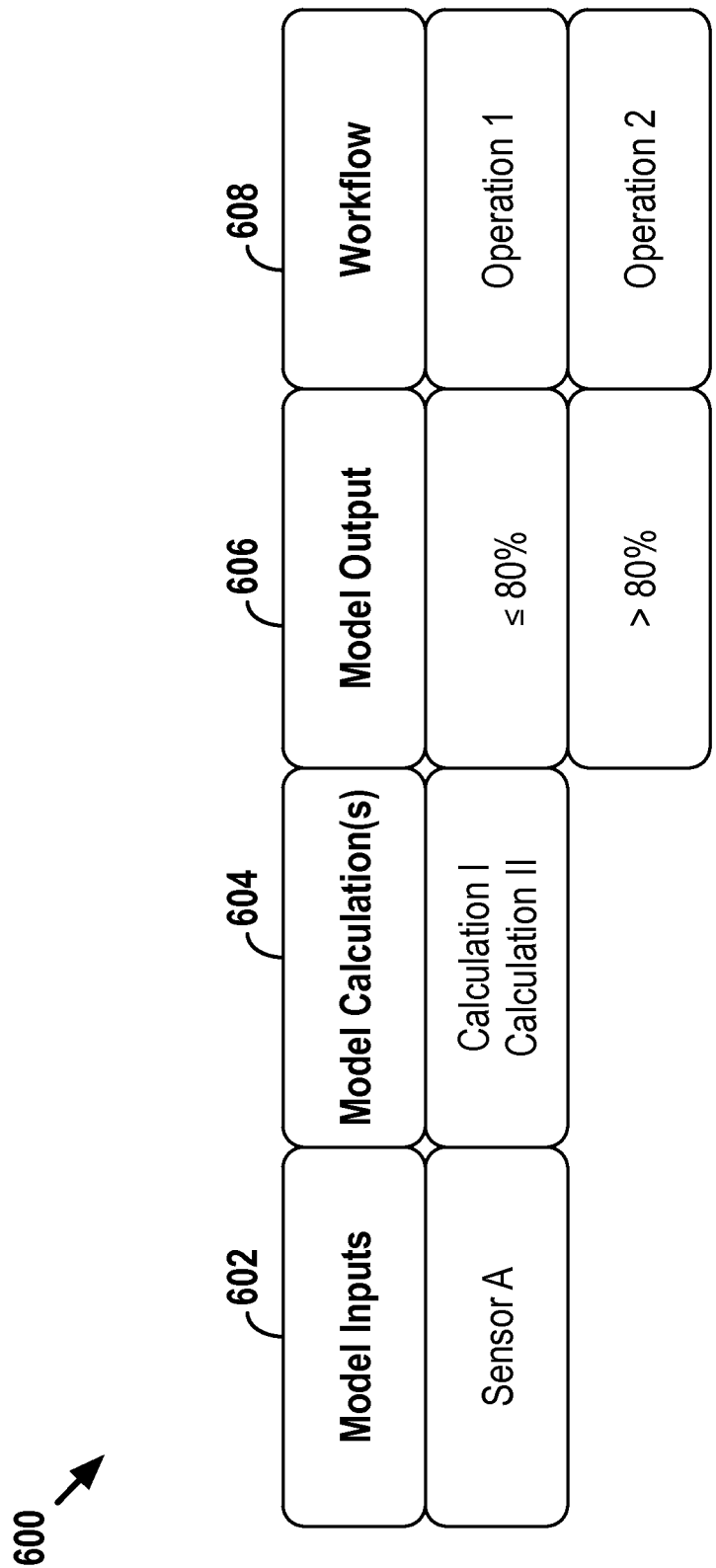
FIG. 6A depicts a conceptual illustration of an aggregate model-workflow pair.

To illustrate, FIG. 6A is a conceptual illustration of an aggregate model-workflow pair 600. As shown, the aggregate model-workflow pair illustration 600 includes a column for model inputs 602, model calculations 604, model output ranges 606, and corresponding workflow operations 608. In this example, the predictive model has a single input, data from Sensor A, and has two calculations, Calculations I and II. The output of this predictive model affects the workflow operation that is performed. If the output probability is less than or equal to 80%, then workflow Operation 1 is performed. Otherwise, the workflow Operation 2 is performed. Other example model-workflow pairs are possible and contemplated herein.

2. Individualized Models & Workflows

In another aspect, the analytics system 108 may be configured to define individualized predictive models and/or workflows for assets, which may involve utilizing the aggregate model-workflow pair as a baseline. The individualization may be based on certain characteristics of assets. In this way, the analytics system 108 may provide a given asset a more accurate and robust model-workflow pair compared to the aggregate model-workflow pair.

In particular, returning to FIG. 5, at block 508, the analytics system 108 may be configured to decide whether to individualize the aggregate model defined at block 504 for a given asset, such as the asset 102. The analytics system 108 may carry out this decision in a number of manners.

In some cases, the analytics system 108 may be configured to define individualized predictive models by default. In other cases, the analytics system 108 may be configured to decide whether to define an individualized predictive model based on certain characteristics of the asset 102. For example, in some cases, only assets of certain types or classes, or operated in certain environments, or that have certain health scores may receive an individualized predictive model. In yet other cases, a user may define whether an individualized model is defined for the asset 102. Other examples are also possible.

In any event, if the analytics system 108 decides to define an individualized predictive model for the asset 102, the analytics system 108 may do so at block 510. Otherwise, the analytics system 108 may proceed to block 512.

At block 510, the analytics system 108 may be configured to define an individualized predictive model in a number of manners. In example implementations, the analytics system 108 may define an individualized predictive model based at least in part on one or more characteristics of the asset 102.

Before defining the individualized predictive model for the asset 102, the analytics system 108 may have determined one or more asset characteristics of interest that form the basis of individualized models. In practice, different predictive models may have different corresponding characteristics of interest.

In general, the characteristics of interest may be characteristics that are related to the aggregate model-workflow pair. For instance, the characteristics of interest may be characteristics that the analytics system 108 has determined influence the accuracy of the aggregate model-workflow pair. Examples of such characteristics may include asset age, asset usage, asset capacity, asset load, asset health (perhaps indicated by an asset health metric, discussed below), asset class (e.g., brand and/or model), and environment in which an asset is operated, among other characteristics.

The analytics system 108 may have determined the characteristics of interest in a number of manners. In one example, the analytics system 108 may have done so by performing one or more modeling simulations that facilitate identifying the characteristics of interest. In another example, the characteristics of interest may have been predefined and stored in the data storage of the analytics system 108. In yet another example, characteristics of interest may have been define by a user and provided to the analytics system 108 via the output system 110. Other examples are also possible.

In any event, after determining the characteristics of interest, the analytics system 108 may determine characteristics of the asset 102 that correspond to the determined characteristics of interest. That is, the analytics system 108 may determine a type, value, existence or lack thereof, etc. of the asset 102's characteristics that correspond to the characteristics of interest. The analytics system 108 may perform this operation in a number of manners.

For examples, the analytics system 108 may be configured to perform this operation based on data originating from the asset 102 and/or the data source 112. In particular, the analytics system 108 may utilize operating data for the asset 102 and/or external data from the data source 112 to determine one or more characteristics of the asset 102. Other examples are also possible.

Based on the determined one or more characteristics of the asset 102, the analytics system 108 may define an individualized, predictive model by modifying the aggregate model. The aggregate model may be modified in a number of manners. For example, the aggregate model may be modified by changing (e.g., adding, removing, re-ordering, etc.) one or more model inputs, changing one or more sensor and/or actuator measurement ranges that correspond to asset-operating limits (e.g., changing operating limits that correspond to "leading indicator" events), changing one or more model calculations, weighting (or changing a weight of) a variable or output of a calculation, utilizing a modeling technique that differs from that which was utilized to define the aggregate model, and/or utilizing a response variable that differs from that which was utilized to define the aggregate model, among other examples.

Figure 6B:
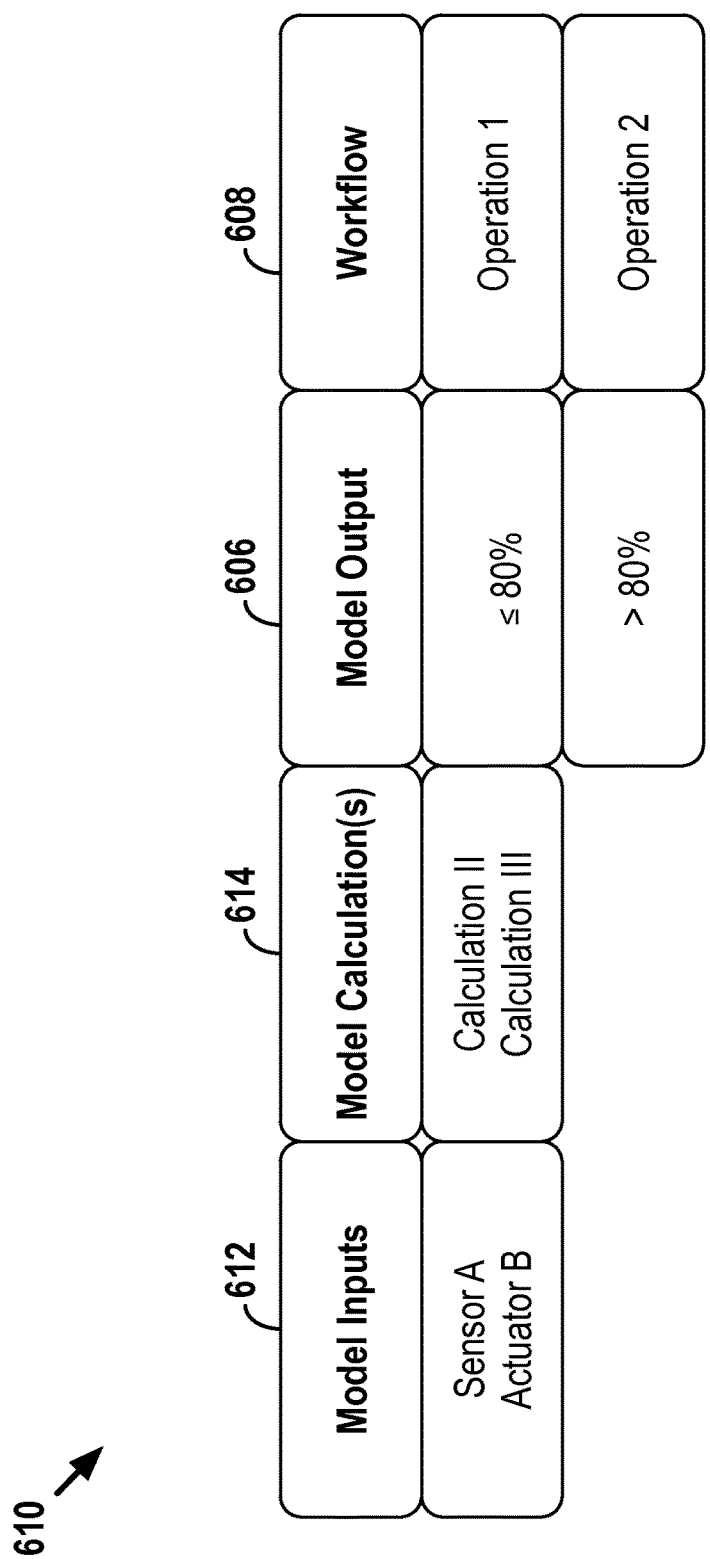
FIG. 6B depicts a conceptual illustration of an individualized model-workflow pair.

To illustrate, FIG. 6B is a conceptual illustration of an individualized model-workflow pair 610. Specifically, the individualized model-workflow pair illustration 610 is a modified version of the aggregate model-workflow pair from FIG. 6A. As shown, the individualized model-workflow pair illustration 610 includes a modified column for model inputs 612 and model calculations 614 and includes the original columns for model output ranges 606 and workflow operations 608 from FIG. 6A. In this example, the individualized model has two inputs, data from Sensor A and Actuator B, and has two calculations, Calculations II and III. The output ranges and corresponding workflow operations are the same as those of FIG. 6A. The analytics system 108 may have defined the individualized model in this way based on determining that the asset 102 is, for example, relatively old and has relatively poor health, among other reasons.

In practice, individualizing the aggregate model may depend on the one or more characteristics of the given asset. In particular, certain characteristics may affect the modification of the aggregate model differently than other characteristics. Further, the type, value, existence, or the like of a characteristic may affect the modification as well. For example, the asset age may affect a first part of the aggregate model, while an asset class may affect a second, different part of the aggregate model. And an asset age within a first range of ages may affect the first part of the aggregate model in a first manner, while an asset age within a second range of ages, different from the first range, may affect the first part of the aggregate model in a second, different manner. Other examples are also possible.

In some implementations, individualizing the aggregate model may depend on considerations in addition to or alternatively to asset characteristics. For instance, the aggregate model may be individualized based on sensor and/or actuator readings of an asset when the asset is known to be in a relatively good operating state (e.g., as defined by a mechanic or the like). More particularly, in an example of a leading-indicator predictive model, the analytics system 108 may be configured to receive an indication that the asset is in a good operating state (e.g., from a computing device operated by a mechanic) along with operating data from the asset. Based at least on the operating data, the analytics system 108 may then individualize the leading-indicator predictive model for the asset by modifying respective operating limits corresponding to "leading indicator" events. Other examples are also possible.

Returning to FIG. 5, at block 512, the analytics system 108 may also be configured to decide whether to individualize a workflow for the asset 102. The analytics system 108 may carry out this decision in a number of manners. In some implementations, the analytics system 108 may perform this operation in line with block 508. In other implementations, the analytics system 108 may decide whether to define an individualized workflow based on the individualized predictive model. In yet another implementation, the analytics system 108 may decide to define an individualized workflow if an individualized predictive model was defined. Other examples are also possible.

In any event, if the analytics system 108 decides to define an individualized workflow for the asset 102, the analytics system 108 may do so at block 514. Otherwise, the analytics system 108 may end the definition phase.

At block 514, the analytics system 108 may be configured to define an individualized workflow in a number of manners. In example implementations, the analytics system 108 may define an individualized workflow based at least in part on one or more characteristics of the asset 102.

Before defining the individualized workflow for the asset 102, similar to defining the individualized predictive model, the analytics system 108 may have determined one or more asset characteristics of interest that form the basis of an individualized workflow, which may have been determined in line with the discussion of block 510. In general, these characteristics of interest may be characteristics that affect the efficacy of the aggregate workflow. Such characteristics may include any of the example characteristics discussed above. Other characteristics are possible as well.

Similar again to block 510, the analytics system 108 may determine characteristics of the asset 102 that correspond to the determined characteristics of interest for an individualized workflow. In example implementations, the analytics system 108 may determine characteristics of the asset 102 in a manner similar to the characteristic determination discussed with reference to block 510 and in fact, may utilize some or all of that determination.

In any event, based on the determined one or more characteristics of the asset 102, the analytics system 108 may individualize a workflow for the asset 102 by modifying the aggregate workflow. The aggregate workflow may be modified in a number of manners. For example, the aggregate workflow may be modified by changing (e.g., adding, removing, re-ordering, replacing, etc.) one or more workflow operations (e.g., changing from a first data-acquisition scheme to a second scheme or changing from a particular data-acquisition scheme to a particular local diagnostic tool) and/or changing (e.g., increasing, decreasing, adding to, removing from, etc.) the corresponding model output value or range of values that triggers particular workflow operations, among other examples. In practice, modification to the aggregate workflow may depend on the one or more characteristics of the asset 102 in a manner similar to the modification to the aggregate model.

Figure 6C:
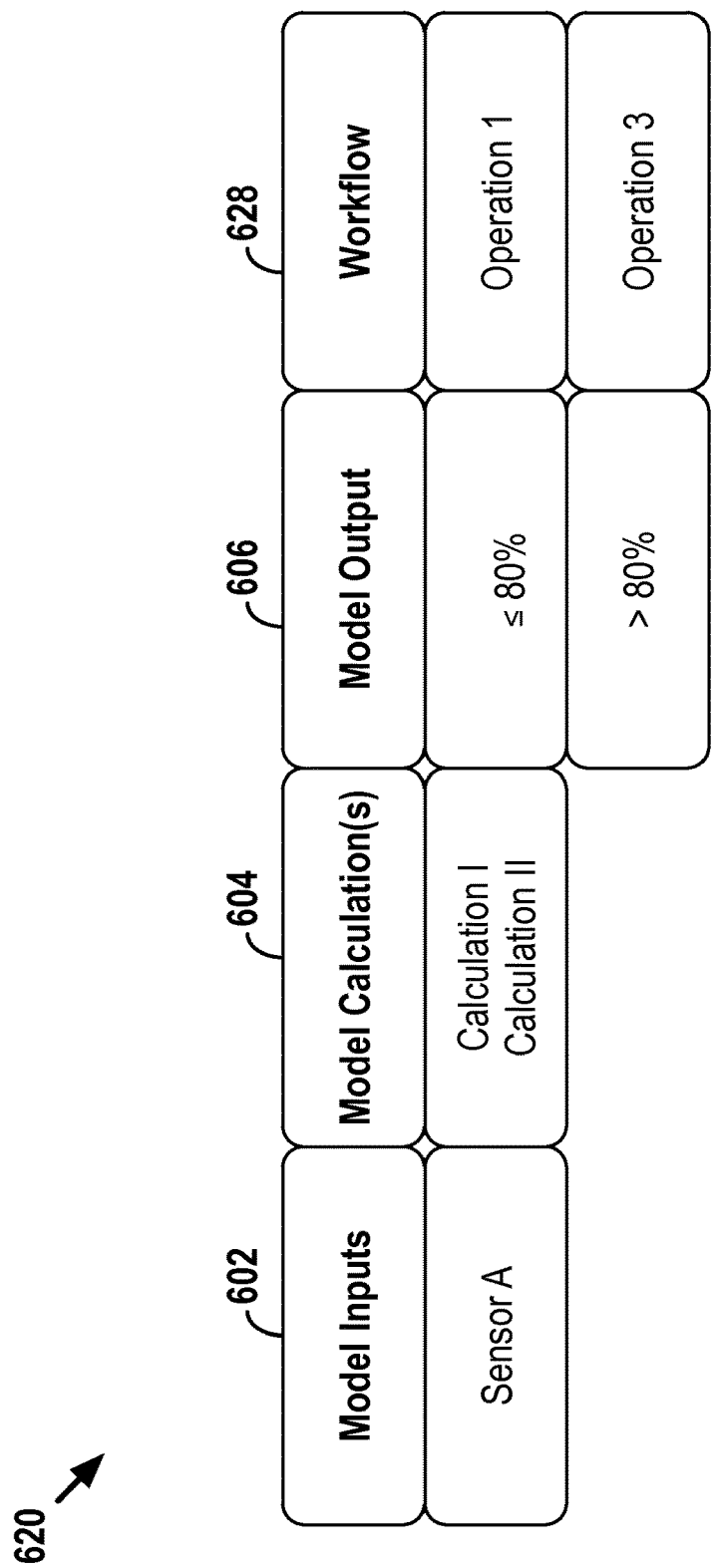
FIG. 6C depicts a conceptual illustration of another individualized model-workflow pair.

To illustrate, FIG. 6C is a conceptual illustration of an individualized model-workflow pair 620. Specifically, the individualized model-workflow pair illustration 620 is a modified version of the aggregate model-workflow pair from FIG. 6A. As shown, the individualized model-workflow pair illustration 620 includes the original columns for model inputs 602, model calculations 604, and model output ranges 606 from FIG. 6A, but includes a modified column for workflow operations 628. In this example, the individualized model-workflow pair is similar to the aggregate model-workflow pair from FIG. 6A, except that when the output of the aggregate model is greater than 80% workflow Operation 3 is triggered instead of Operation 1. The analytics system 108 may have defined this individual workflow based on determining that the asset 102, for example, operates in an environment that historically increases the occurrence of asset failures, among other reasons.

After defining the individualized workflow, the analytics system 108 may end the definition phase. At that point, the analytics system 108 may then have an individualized model-workflow pair for the asset 102.

In some example implementations, the analytics system 108 may be configured to define an individualized predictive model and/or corresponding workflow for a given asset without first defining an aggregate predictive model and/or corresponding workflow. Other examples are also possible.

3. Health-Score Models & Workflows

In a particular implementation, as mentioned above, the analytics system 108 may be configured to define predictive models and corresponding workflows associated with the health of assets. In example implementations, one or more predictive models for monitoring the health of an asset may be utilized to output a health metric (e.g., "health score") for an asset, which is a single, aggregated metric that indicates whether a failure will occur at a given asset within a given timeframe into the future (e.g., the next two weeks). In particular, a health metric may indicate a likelihood that no failures from a group of failures will occur at an asset within a given timeframe into the future, or a health metric may indicate a likelihood that at least one failure from a group of failures will occur at an asset within a given timeframe into the future.

In practice, the predictive models utilized to output a health metric and the corresponding workflows may be defined as aggregate or individualized models and/or workflows, in line with the above discussion.

Moreover, depending on the desired granularity of the health metric, the analytics system 108 may be configured to define different predictive models that output different levels of health metrics and to define different corresponding workflows. For example, the analytics system 108 may define a predictive model that outputs a health metric for the asset as a whole (i.e., an asset-level health metric). As another example, the analytics system 108 may define a respective predictive model that outputs a respective health metric for one or more subsystems of the asset (i.e., subsystem-level health metrics). In some cases, the outputs of each subsystem-level predictive model may be combined to generate an asset-level health metric. Other examples are also possible.

Figure 7:
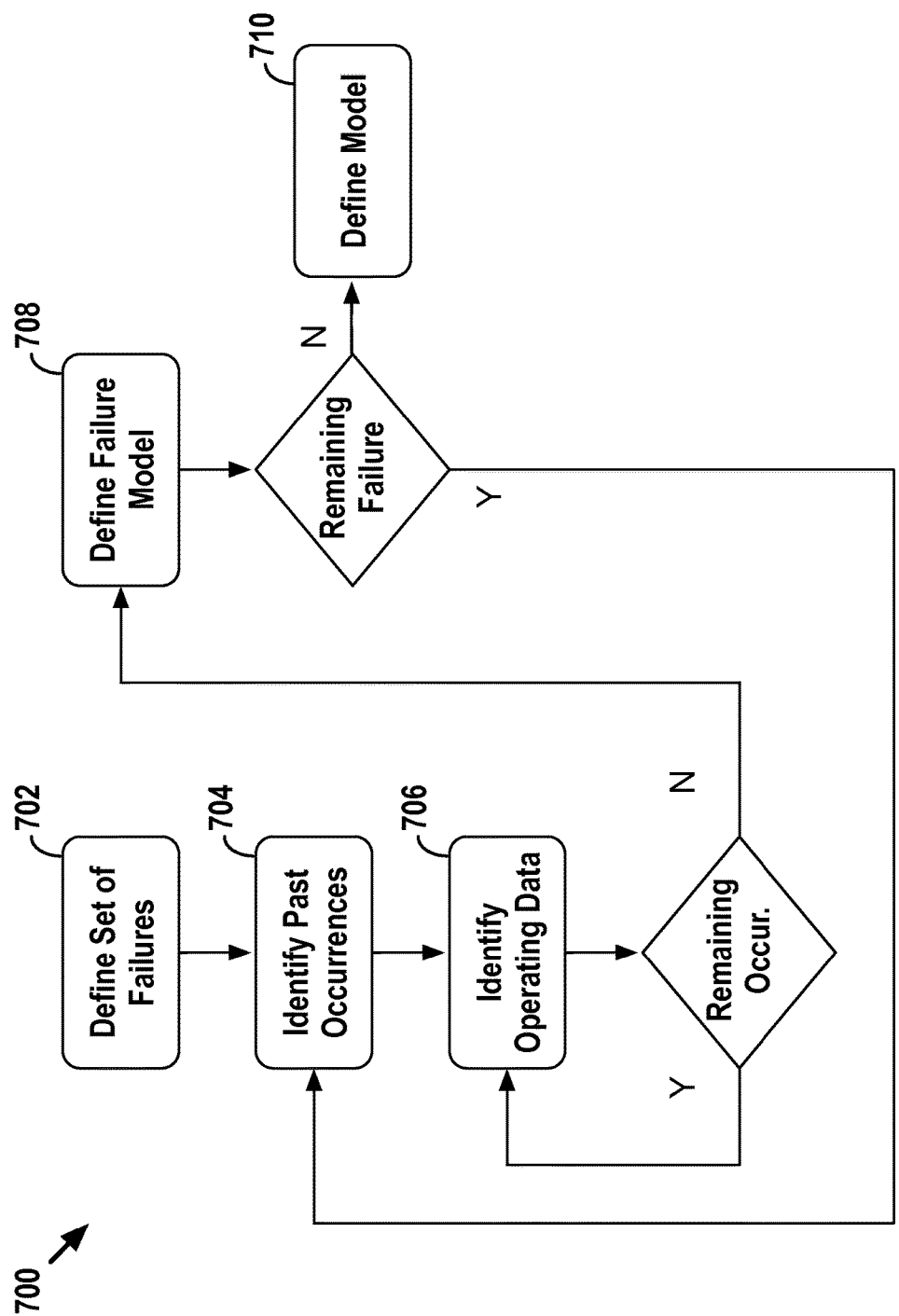
FIG. 7 depicts an example flow diagram of a modeling phase that may be used for defining a predictive model that outputs a health metric.

In general, defining a predictive model that outputs a health metric may be performed in a variety of manners. FIG. 7 is a flow diagram 700 depicting one possible example of a modeling phase that may be used for defining a model that outputs a health metric. For purposes of illustration, the example modeling phase is described as being carried out by the analytics system 108, but this modeling phase may be carried out by other systems as well. One of ordinary skill in the art will appreciate that the flow diagram 700 is provided for sake of clarity and explanation and that numerous other combinations of operations may be utilized to determine a health metric.

As shown in FIG. 7, at block 702, the analytics system 108 may begin by defining a set of the one or more failures that form the basis for the health metric (i.e., the failures of interest). In practice, the one or more failures may be those failures that could render an asset (or a subsystem thereof) inoperable if they were to occur. Based on the defined set of failures, the analytics system 108 may take steps to define a model for predicting a likelihood of any of the failures occurring within a given timeframe in the future (e.g., the next two weeks).

In particular, at block 704, the analytics system 108 may analyze historical operating data for a group of one or more assets to identify past occurrences of a given failure from the set of failures. At block 706, the analytics system 108 may identify a respective set of operating data that is associated with each identified past occurrence of the given failure (e.g., sensor and/or actuator data from a given timeframe prior to the occurrence of the given failure). At block 708, the analytics system 108 may analyze the identified sets of operating data associated with past occurrences of the given failure to define a relationship (e.g., a failure model) between (1) the values for a given set of operating metrics and (2) the likelihood of the given failure occurring within a given timeframe in the future (e.g., the next two weeks). Lastly, at block 710, the defined relationship for each failure in the defined set (e.g., the individual failure models) may then be combined into a model for predicting the overall likelihood of a failure occurring.

As the analytics system 108 continues to receive updated operating data for the group of one or more assets, the analytics system 108 may also continue to refine the predictive model for the defined set of one or more failures by repeating steps 704-710 on the updated operating data.

The functions of the example modeling phase illustrated in FIG. 7 will now be described in further detail. Starting with block 702, as noted above, the analytics system 108 may begin by defining a set of the one or more failures that form the basis for the health metric. The analytics system 108 may perform this function in various manners.

In one example, the set of the one or more failures may be based on one or more user inputs. Specifically, the analytics system 108 may receive from a computing system operated by a user, such as the output system 110, input data indicating a user selection of the one or more failures. As such, the set of one or more failures may be user-defined.

In other examples, the set of the one or more failures may be based on a determination made by the analytics system 108 (e.g., machine-defined). In particular, the analytics system 108 may be configured to define the set of one or more failures, which may occur in a number of manners.

For instance, the analytics system 108 may be configured to define the set of failures based on one or more characteristics of the asset 102. That is, certain failures may correspond to certain characteristics, such as asset type, class, etc., of an asset. For example, each type and/or class of asset may have respective failures of interest.

In another instance, the analytics system 108 may be configured to define the set of failures based on historical data stored in the databases of the analytics system 108 and/or external data provided by the data source 112. For example, the analytics system 108 may utilize such data to determine which failures result in the longest repair-time and/or which failures are historically followed by additional failures, among other examples.

In yet other examples, the set of one or more failures may be defined based on a combination of user inputs and determinations made by the analytics system 108. Other examples are also possible.

At block 704, for each of the failures from the set of failures, the analytics system 108 may analyze historical operating data for a group of one or more assets (e.g., abnormal-behavior data) to identify past occurrences of a given failure. The group of the one or more assets may include a single asset, such as asset 102, or multiple assets of a same or similar type, such as fleet of assets that includes the assets 102 and 104. The analytics system 108 may analyze a particular amount of historical operating data, such as a certain amount of time's worth of data (e.g., a month's worth) or a certain number of data-points (e.g., the most recent thousand data-points), among other examples.

In practice, identifying past occurrences of the given failure may involve the analytics system 108 identifying the type of operating data, such as abnormal-condition data, that indicates the given failure. In general, a given failure may be associated with one or multiple abnormal-condition indicators, such as fault codes. That is, when the given failure occurs, one or multiple abnormal-condition indicators may be triggered. As such, abnormal-condition indicators may be reflective of an underlying symptom of a given failure.

After identifying the type of operating data that indicates the given failure, the analytics system 108 may identify the past occurrences of the given failure in a number of manners. For instance, the analytics system 108 may locate, from historical operating data stored in the databases of the analytics system 108, abnormal-condition data corresponding to the abnormal-condition indicators associated with the given failure. Each located abnormal-condition data would indicate an occurrence of the given failure. Based on this located abnormal-condition data, the analytics system 108 may identify a time at which a past failure occurred.

At block 706, the analytics system 108 may identify a respective set of operating data that is associated with each identified past occurrence of the given failure. In particular, the analytics system 108 may identify a set of sensor and/or actuator data from a certain timeframe around the time of the given occurrence of the given failure. For example, the set of data may be from a particular timeframe (e.g., two weeks) before, after, or around the given occurrence of the failure. In other cases, the set of data may be identified from a certain number of data-points before, after, or around the given occurrence of the failure.

In example implementations, the set of operating data may include sensor and/or actuator data from some or all of the sensors and actuators of the asset 102. For example, the set of operating data may include data from sensors and/or actuators associated with an abnormal-condition indicator corresponding to the given failure.

Figure 8:
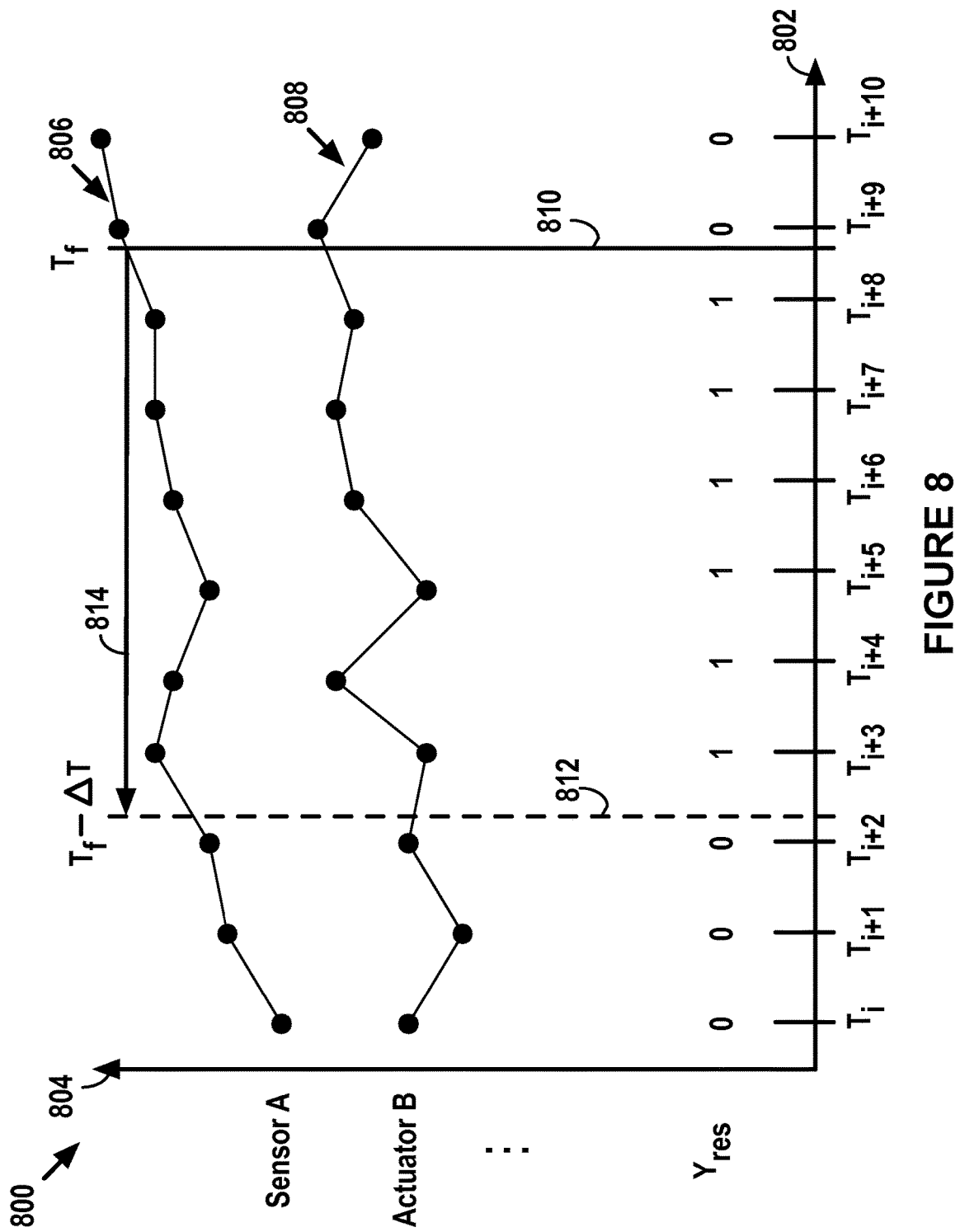
FIG. 8 depicts a conceptual illustration of data utilized to define a model.

To illustrate, FIG. 8 depicts a conceptual illustration of historical operating data that the analytics system 108 may analyze to facilitate defining a model. Plot 800 may correspond to a segment of historical data that originated from some (e.g., Sensor A and Actuator B) or all of the sensors and actuators of the asset 102. As shown, the plot 800 includes time on the x-axis 802, measurement values on the y-axis 804, and sensor data 806 corresponding to Sensor A and actuator data 808 corresponding to Actuator B, each of which includes various data-points representing measurements at particular points in time, $T_i$. Moreover, the plot 800 includes an indication of an occurrence of a failure 810 that occurred at a past time, $T_f$ (e.g., "time of failure"), and an indication of an amount of time 812 before the occurrence of the failure, $\Delta T$, from which sets of operating data are identified. As such, $T_f$-$\Delta T$ defines a timeframe 814 of data-points of interest.

Returning to FIG. 7, after the analytics system 108 identifies the set of operating data for the given occurrence of the given failure (e.g., the occurrence at $T_f$), the analytics system 108 may determine whether there are any remaining occurrences for which a set of operating data should be identified. In the event that there is a remaining occurrence, block 706 would be repeated for each remaining occurrence.

Thereafter, at block 708, the analytics system 108 may analyze the identified sets of operating data associated with the past occurrences of the given failure to define a relationship (e.g., a failure model) between (1) a given set of operating metrics (e.g., a given set of sensor and/or actuator measurements) and (2) the likelihood of the given failure occurring within a given timeframe in the future (e.g., the next two weeks). That is, a given failure model may take as inputs sensor and/or actuator measurements from one or more sensors and/or actuators and output a probability that the given failure will occur within the given timeframe in the future.

In general, a failure model may define a relationship between operating conditions of the asset 102 and the likelihood of a failure occurring. In some implementations, in addition to raw data signals from sensors and/or actuators of the asset 102, a failure model may receive a number of other data inputs, also known as features, which are derived from the sensor and/or actuator signals. Such features may include an average or range of values that were historically measured when a failure occurred, an average or range of value gradients (e.g., a rate of change in measurements) that were historically measured prior to an occurrence of a failure, a duration of time between failures (e.g., an amount of time or number of data-points between a first occurrence of a failure and a second occurrence of a failure), and/or one or more failure patterns indicating sensor and/or actuator measurement trends around the occurrence of a failure. One of ordinary skill in the art will appreciate that these are but a few example features that can be derived from sensor and/or actuator signals and that numerous other features are possible.

In practice, a failure model may be defined in a number of manners. In example implementations, the analytics system 108 may define a failure model by utilizing one or more modeling techniques that return a probability between zero and one, which may take the form of any modeling techniques described above.

In a particular example, defining a failure model may involve the analytics system 108 generating a response variable based on the historical operating data identified at block 706. Specifically, the analytics system 108 may determine an associated response variable for each set of sensor and/or actuator measurements received at a particular point in time. As such, the response variable may take the form of a data set associated with the failure model.

The response variable may indicate whether the given set of measurements is within any of the timeframes determined at block 706. That is, a response variable may reflect whether a given set of data is from a time of interest about the occurrence of a failure. The response variable may be a binary-valued response variable such that, if the given set of measurements is within any of determined timeframes, the associated response variable is assigned a value of one, and otherwise, the associated response variable is assigned a value of zero.

Returning to FIG. 8, a conceptual illustration of a response variable vector, $Y_{res}$ is shown on the plot 800. As shown, response variables associated with sets of measurements that are within the timeframe 814 have a value of one (e.g., $Y_{res}$ at times $T_{i+3}$-$T_{i+8}$), while response variables associated with sets of measurements outside the timeframe 814 have a value of zero (e.g., $Y_{res}$ at times $T_i$-$T_{i+2}$ and $T_{i+9}$-$T_{i+10}$). Other response variables are also possible.

Continuing in the particular example of defining a failure model based on a response variable, the analytics system 108 may train the failure model with the historical operating data identified at block 706 and the generated response variable. Based on this training process, the analytics system 108 may then define the failure model that receives as inputs various sensor and/or actuator data and outputs a probability between zero and one that a failure will occur within a period of time equivalent to the timeframe used to generate the response variable.

In some cases, training with the historical operating data identified at block 706 and the generated response variable may result in variable importance statistics for each sensor and/or actuator. A given variable importance statistic may indicate the sensor's or actuator's relative effect on the probability that a given failure will occur within the period of time into the future.

Additionally or alternatively, the analytics system 108 may be configured to define a failure model based on one or more survival analysis techniques, such as a Cox proportional hazard technique. The analytics system 108 may utilize a survival analysis technique in a manner similar in some respects to the above-discussed modeling technique, but the analytics system 108 may determine a survival time-response variable that indicates an amount of time from the last failure to a next expected event. A next expected event may be either reception of senor and/or actuator measurements or an occurrence of a failure, whichever occurs first. This response variable may include a pair of values that are associated with each of the particular points in time at which measurements are received. The response variable may then be utilized to determine a probability that a failure will occur within the given timeframe in the future.

In some example implementations, the failure model may be defined based in part on external data, such as weather data, and "hotbox" data, among other data. For instance, based on such data, the failure model may increase or decrease an output failure probability.

In practice, external data may be observed at points in time that do not coincide with times at which asset sensors and/or actuators obtain measurements. For example, the times at which "hotbox" data is collected (e.g., times at which a locomotive passes along a section of railroad track that is outfitted with hot box sensors) may be in disagreement with sensor and/or actuator measurement times. In such cases, the analytics system 108 may be configured to perform one or more operations to determine external data observations that would have been observed at times that correspond to the sensor measurement times.

Specifically, the analytics system 108 may utilize the times of the external data observations and times of the measurements to interpolate the external data observations to produce external data values for times corresponding to the measurement times. Interpolation of the external data may allow external data observations or features derived therefrom to be included as inputs into the failure model. In practice, various techniques may be used to interpolate the external data with the sensor and/or actuator data, such as nearest-neighbor interpolation, linear interpolation, polynomial interpolation, and spline interpolation, among other examples.

Returning to FIG. 7, after the analytics system 108 determines a failure model for a given failure from the set of failures defined at block 702, the analytics system 108 may determine whether there are any remaining failures for which a failure model should be determined. In the event that there remains a failure for which a failure model should be determined, the analytics system 108 may repeat the loop of blocks 704-708. In some implementations, the analytics system 108 may determine a single failure model that encompasses all of the failures defined at block 702. In other implementations, the analytics system 108 may determine a failure model for each subsystem of the asset 102, which may then be utilized to determine an asset-level failure model. Other examples are also possible.

Lastly, at block 710, the defined relationship for each failure in the defined set (e.g., the individual failure models) may then be combined into the model (e.g., the health-metric model) for predicting the overall likelihood of a failure occurring within the given timeframe in the future (e.g., the next two weeks). That is, the model receives as inputs sensor and/or actuator measurements from one or more sensors and/or actuators and outputs a single probability that at least one failure from the set of failures will occur within the given timeframe in the future.

The analytics system 108 may define the health-metric model in a number of manners, which may depend on the desired granularity of the health metric. That is, in instances where there are multiple failure models, the outcomes of the failure models may be utilized in a number of manners to obtain the output of the health-metric model. For example, the analytics system 108 may determine a maximum, median, or average from the multiple failure models and utilize that determined value as the output of the health-metric model.

In other examples, determining the health-metric model may involve the analytics system 108 attributing a weight to individual probabilities output by the individual failure models. For instance, each failure from the set of failures may be considered equally undesirable, and so each probability may likewise be weighted the same in determining the health-metric model. In other instances, some failures may be considered more undesirable than others (e.g., more catastrophic or require longer repair time, etc.), and so those corresponding probabilities may be weighted more than others.

In yet other examples, determining the health-metric model may involve the analytics system 108 utilizing one or more modeling techniques, such as a regression technique. An aggregate response variable may take the form of the logical disjunction (logical OR) of the response variables (e.g., $Y_{res}$ in FIG. 8) from each of the individual failure models. For example, aggregate response variables associated with any set of measurements that occur within any timeframe determined at block 706 (e.g., the timeframe 814 of FIG. 8) may have a value of one, while aggregate response variables associated with sets of measurements that occur outside any of the timeframes may have a value of zero. Other manners of defining the health-metric model are also possible.

In some implementations, block 710 may be unnecessary. For example, as discussed above, the analytics system 108 may determine a single failure model, in which case the health-metric model may be the single failure model.

In practice, the analytics system 108 may be configured to update the individual failure models and/or the overall health-metric model. The analytics system 108 may update a model daily, weekly, monthly, etc. and may do so based on a new portion of historical operating data from the asset 102 or from other assets (e.g., from other assets in the same fleet as the asset 102). Other examples are also possible.

C. Deploying Models & Workflows

After the analytics system 108 defines a model-workflow pair, the analytics system 108 may deploy the defined model-workflow pair to one or more assets. Specifically, the analytics system 108 may transmit the defined predictive model and/or corresponding workflow to at least one asset, such as the asset 102. The analytics system 108 may transmit model-workflow pairs periodically or based on triggering events, such as any modifications or updates to a given model-workflow pair.

In some cases, the analytics system 108 may transmit only one of an individualized model or an individualized workflow. For example, in scenarios where the analytics system 108 defined only an individualized model or workflow, the analytics system 108 may transmit an aggregate version of the workflow or model along with the individualized model or workflow, or the analytics system 108 may not need to transmit an aggregate version if the asset 102 already has the aggregate version stored in data storage. In sum, the analytics system 108 may transmit (1) an individualized model and/or individualized workflow, (2) an individualized model and the aggregate workflow, (3) the aggregate model and an individualized workflow, or (4) the aggregate model and the aggregate workflow.

In practice, the analytics system 108 may have carried out some or all of the operations of blocks 702-710 of FIG. 7 for multiple assets to define model-workflow pairs for each asset. For example, the analytics system 108 may have additionally defined a model-workflow pair for the asset 104. The analytics system 108 may be configured to transmit respective model-workflow pairs to the assets 102 and 104 simultaneously or sequentially.

D. Local Execution by Asset

A given asset, such as the asset 102, may be configured to receive a model-workflow pair or a portion thereof and operate in accordance with the received model-workflow pair. That is, the asset 102 may store in data storage the model-workflow pair and input into the predictive model data obtained by sensors and/or actuators of the asset 102 and at times, execute the corresponding workflow based on the output of the predictive model.

In practice, various components of the asset 102 may execute the predictive model and/or corresponding workflow. For example, as discussed above, each asset may include a local analytics device configured to store and run model-workflow pairs provided by the analytics system 108. When the local analytics device receives particular sensor and/or actuator data, it may input the received data into the predictive model and depending on the output of the model, may execute one or more operations of the corresponding workflow.

In another example, a central processing unit of the asset 102 that is separate from the local analytics device may execute the predictive model and/or corresponding workflow. In yet other examples, the local analytics system and central processing unit of the asset 102 may collaboratively execute the model-workflow pair. For instance, the local analytics system may execute the predictive model and the central processing unit may execute the workflow or vice versa.

In general, an asset executing a predictive model and based on the resulting output, executing operations of the workflow may facilitate determining a cause or causes of the likelihood of a particular event occurring that is output by the model and/or may facilitate preventing a particular event from occurring in the future. In executing a workflow, an asset may locally determine and take actions to help prevent an event from occurring, which may be beneficial in situations when reliance on the analytics system 108 to make such determinations and provide recommended actions is not efficient or feasible (e.g., when there is network latency, when network connection is poor, when the asset moves out of coverage of the communication network 106, etc.).

Figure 9:
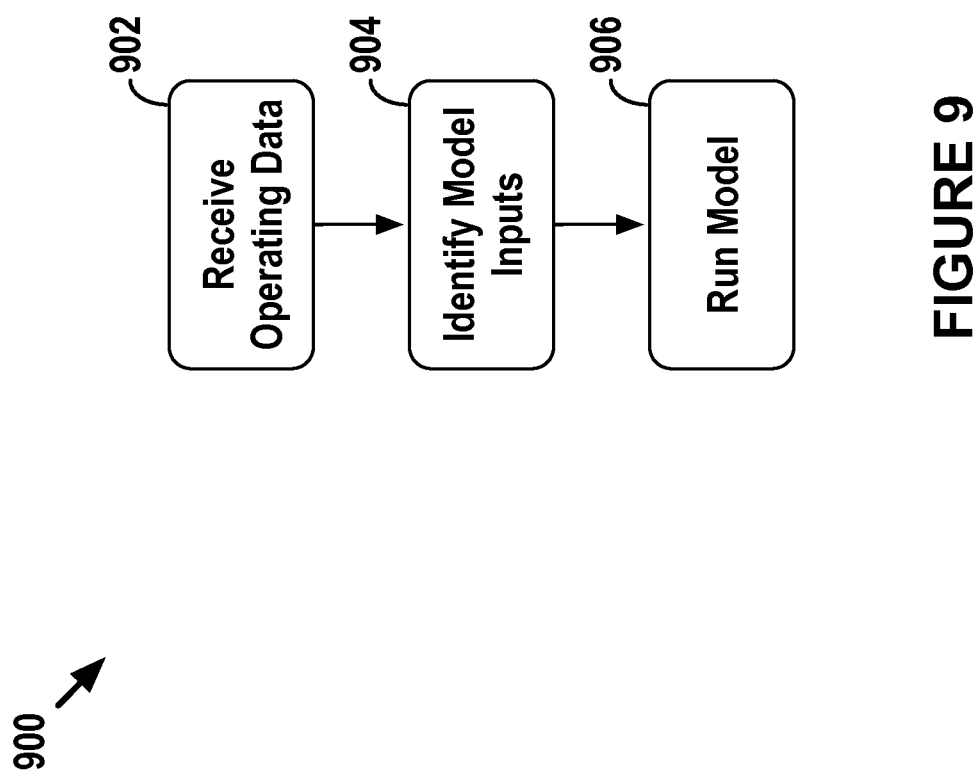
FIG. 9 depicts an example flow diagram of a local-execution phase that may be used for locally executing a predictive model.

In practice, an asset may execute a predictive model in a variety of manners, which may be dependent on the particular predictive model. FIG. 9 is a flow diagram 900 depicting one possible example of a local-execution phase that may be used for locally executing a predictive model. The example local-execution phase will be discussed in the context of a health-metric model that outputs a health metric of an asset, but it should be understood that a same or similar local-execution phase may be utilized for other types of predictive models. Moreover, for purposes of illustration, the example local-execution phase is described as being carried out by a local analytics device of the asset 102, but this phase may be carried out by other devices and/or systems as well. One of ordinary skill in the art will appreciate that the flow diagram 900 is provided for sake of clarity and explanation and that numerous other combinations of operations and functions may be utilized to locally execute a predictive model.

As shown in FIG. 9, at block 902, the local analytics device may receive data that reflects the current operating conditions of the asset 102. At block 904, the local analytics device may identify, from the received data, the set of operating data that is to be input into the model provided by the analytics system 108. At block 906, the local analytics device may then input the identified set of operating data into the model and run the model to obtain a health metric for the asset 102.

As the local analytics device continues to receive updated operating data for the asset 102, the local analytics device may also continue to update the health metric for the asset 102 by repeating the operations of blocks 902-906 based on the updated operating data. In some cases, the operations of blocks 902-906 may be repeated each time the local analytics device receives new data from sensors and/or actuators of the asset 102 or periodically (e.g., hourly, daily, weekly, monthly, etc.). In this way, local analytics devices may be configured to dynamically update health metrics, perhaps in real-time, as assets are used in operation.

The functions of the example local-execution phase illustrated in FIG. 9 will now be described in further detail. At block 902, the local analytics device may receive data that reflects the current operating conditions of the asset 102. Such data may include sensor data from one or more of the sensors of the asset 102, actuator data from one or more actuators of the asset 102, and/or it may include abnormal-condition data, among other types of data.

At block 904, the local analytics device may identify, from the received data, the set of operating data that is to be input into the health-metric model provided by the analytics system 108. This operation may be performed in a number of manners.

In one example, the local analytics device may identify the set of operating data inputs (e.g., data from particular sensors and/or actuators of interest) for the model based on a characteristic of the asset 102, such as asset type or asset class, for which the health metric is being determined. In some cases, the identified set of operating data inputs may be sensor data from some or all of the sensors of the asset 102 and/or actuator data from some of all of the actuators of the asset 102.

In another example, the local analytics device may identify the set of operating data inputs based on the predictive model provided by the analytics system 108. That is, the analytics system 108 may provide some indication to the asset 102 (e.g., either in the predictive model or in a separate data transmission) of the particular inputs for the model. Other examples of identifying the set of operating data inputs are also possible.

At block 906, the local analytics device may then run the health-metric model. Specifically, the local analytics device may input the identified set of operating data into the model, which in turn determines and outputs an overall likelihood of at least one failure occurring within the given timeframe in the future (e.g., the next two weeks).

In some implementations, this operation may involve the local analytics device inputting particular operating data (e.g., sensor and/or actuator data) into one or more individual failure models of the health-metric model, which each may output an individual probability. The local analytics device may then use these individual probabilities, perhaps weighting some more than others in accordance with the health-metric model, to determine the overall likelihood of a failure occurring within the given timeframe in the future.

After determining the overall likelihood of a failure occurring, the local analytics device may convert the probability of a failure occurring into the health metric that may take the form of a single, aggregated parameter that reflects the likelihood that no failures will occur at the asset 102 within the give timeframe in the future (e.g., two weeks). In example implementations, converting the failure probability into the health metric may involve the local analytics device determining the complement of the failure probability. Specifically, the overall failure probability may take the form of a value ranging from zero to one; the health metric may be determined by subtracting one by that number. Other examples of converting the failure probability into the health metric are also possible.

After an asset locally executes a predictive model, the asset may then execute a corresponding workflow based on the resulting output of the executed predictive model. As mentioned above, workflows may take various forms and so, workflows may be executed in a variety of manners.

For example, the asset 102 may internally execute one or more operations that modify some behavior of the asset 102, such as modifying a data-acquisition and/or -transmission scheme, executing a local diagnostic tool, modifying an operating condition of the asset 102 (e.g., modifying a velocity, acceleration, fan speed, propeller angle, air intake, etc. via one or more actuators of the asset 102), or outputting an indication, perhaps of a relatively low health metric or of recommended preventative actions that should be executed in relation to the asset 102, at a user interface of the asset 102 or to an external computing system.

In another example, the asset 102 may transmit to a system on the communication network 106, such as the output system 110, an instruction to cause the system to carry out an operation, such as generating a work-order or ordering a particular part for a repair of the asset 102. Other examples of the asset 102 locally executing a workflow are also possible.

E. Model/Workflow Modification Phase

In another aspect, the analytics system 108 may carry out a modification phase during which the analytics system 108 modifies a deployed model and/or workflow based on new asset data. This phase may be performed for both aggregate and individualized models and workflows.

In particular, as a given asset (e.g., the asset 102) operates in accordance with a model-workflow pair, the asset 102 may provide operating data to the analytics system 108 and/or the data source 112 may provide to the analytics system 108 external data related to the asset 102. Based at least on this data, the analytics system 108 may modify the model and/or workflow for the asset 102 and/or the model and/or workflow for other assets, such as the asset 104. In modifying models and/or workflows for other assets, the analytics system 108 may share information learned from the behavior of the asset 102.

Figure 10:
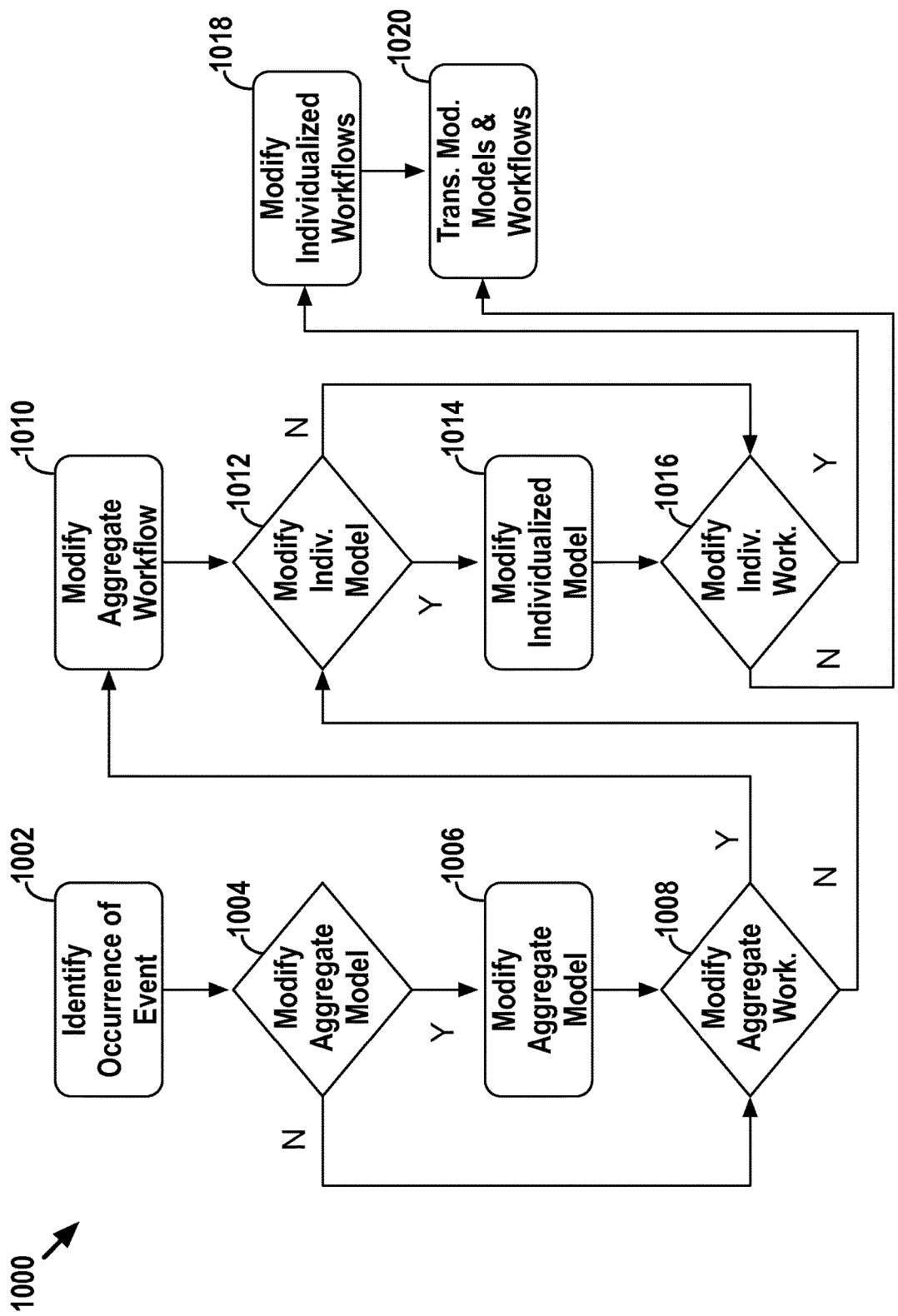
FIG. 10 depicts an example flow diagram of a modification phase that may be used for modifying model-workflow pairs.

In practice, the analytics system 108 may make modifications in a number of manners. FIG. 10 is a flow diagram 1000 depicting one possible example of a modification phase that may be used for modifying model-workflow pairs. For purposes of illustration, the example modification phase is described as being carried out by the analytics system 108, but this modification phase may be carried out by other systems as well. One of ordinary skill in the art will appreciate that the flow diagram 1000 is provided for sake of clarity and explanation and that numerous other combinations of operations may be utilized to modify model-workflow pairs.

As shown in FIG. 10, at block 1002, the analytics system 108 may receive data from which the analytics system 108 identifies an occurrence of a particular event. The data may be operating data originating from the asset 102 or external data related to the asset 102 from the data source 112, among other data. The event may take the form of any of the events discussed above, such as a failure at the asset 102.

In other example implementations, the event may take the form of a new component or subsystem being added to the asset 102. Another event may take the form of a "leading indicator" event, which may involve sensors and/or actuators of the asset 102 generating data that differs, perhaps by a threshold differential, from the data identified at block 706 of FIG. 7 during the model-definition phase. This difference may indicate that the asset 102 has operating conditions that are above or below normal operating conditions for assets similar to the asset 102. Yet another event may take the form of an event that is followed by one or more leading indicator events.

Based on the identified occurrence of the particular event and/or the underlying data (e.g., operating data and/or external data related to the asset 102), the analytics system 108 may then modify the aggregate, predictive model and/or workflow and/or one or more individualized predictive models and/or workflows. In particular, at block 1004, the analytics system 108 may determine whether to modify the aggregate, predictive model. The analytics system 108 may determine to modify the aggregate, predictive model for a number of reasons.

For example, the analytics system 108 may modify the aggregate, predictive model if the identified occurrence of the particular event was the first occurrence of this particular event for a plurality of assets including the asset 102, such as the first time a particular failure occurred at an asset from a fleet of assets or the first time a particular new component was added to an asset from a fleet of assets.

In another example, the analytics system 108 may make a modification if data associated with the identified occurrence of the particular event is different from data that was utilized to originally define the aggregate model. For instance, the identified occurrence of the particular event may have occurred under operating conditions that had not previously been associated with an occurrence of the particular event (e.g., a particular failure might have occurred with associated sensor values not previously measured before with the particular failure). Other reasons for modifying the aggregate model are also possible.

If the analytics system 108 determines to modify the aggregate, predictive model, the analytics system 108 may do so at block 1006. Otherwise, the analytics system 108 may proceed to block 1008.

At block 1006, the analytics system 108 may modify the aggregate model based at least in part on the data related to the asset 102 that was received at block 1002. In example implementations, the aggregate model may be modified in various manners, such as any manner discussed above with reference to block 510 of FIG. 5. In other implementations, the aggregate model may be modified in other manners as well.

At block 1008, the analytics system 108 may then determine whether to modify the aggregate workflow. The analytics system 108 may modify the aggregate workflow for a number of reasons.

For example, the analytics system 108 may modify the aggregate workflow based on whether the aggregate model was modified at block 1004 and/or if there was some other change at the analytics system 108. In other examples, the analytics system 108 may modify the aggregate workflow if the identified occurrence of the event at block 1002 occurred despite the asset 102 executing the aggregate workflow. For instance, if the workflow was aimed to help facilitate preventing the occurrence of the event (e.g., a failure) and the workflow was executed properly but the event still occurred nonetheless, then the analytics system 108 may modify the aggregate workflow. Other reasons for modifying the aggregate workflow are also possible.

If the analytics system 108 determines to modify the aggregate workflow, the analytics system 108 may do so at block 1010. Otherwise, the analytics system 108 may proceed to block 1012.

At block 1010, the analytics system 108 may modify the aggregate workflow based at least in part on the data related to the asset 102 that was received at block 1002. In example implementations, the aggregate workflow may be modified in various manners, such as any manner discussed above with reference to block 514 of FIG. 5. In other implementations, the aggregate model may be modified in other manners as well.

At blocks 1012 through blocks 1018, the analytics system 108 may be configured to modify one or more individualized models (e.g., for each of assets 102 and 104) and/or one or more individualized workflows (e.g., for one of asset 102 or asset 104) based at least in part on the data related to the asset 102 that was received at block 1002. The analytics system 108 may do so in a manner similar to blocks 1004-1010.

However, the reasons for modifying an individualized model or workflow may differ from the reasons for the aggregate case. For instance, the analytics system 108 may further consider the underlying asset characteristics that were utilized to define the individualized model and/or workflow in the first place. In a particular example, the analytics system 108 may modify an individualized model and/or workflow if the identified occurrence of the particular event was the first occurrence of this particular event for assets with asset characteristics of the asset 102. Other reasons for modifying an individualized model and/or workflow are also possible.

Figure 6D:
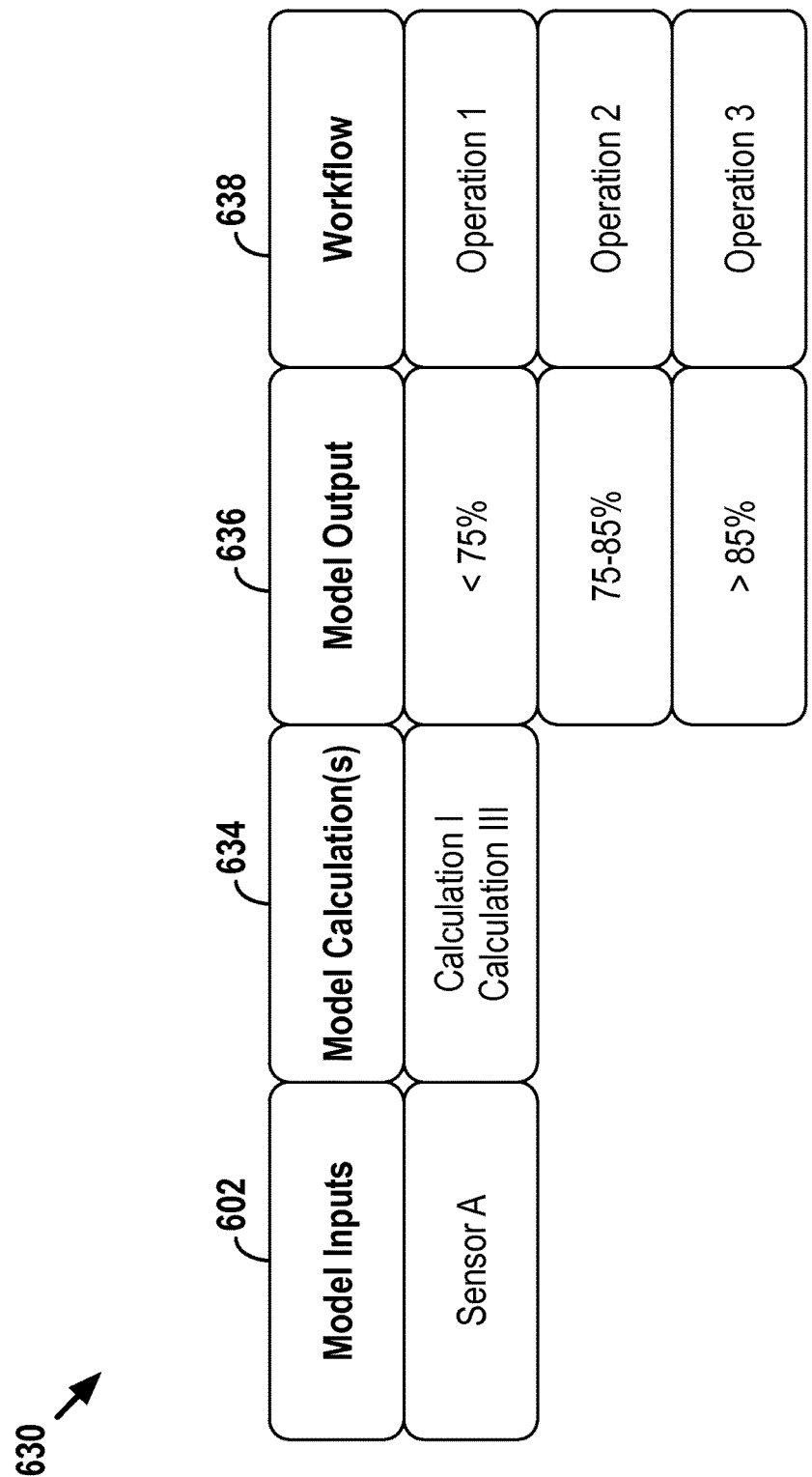
FIG. 6D depicts a conceptual illustration of a modified model-workflow pair.

To illustrate, FIG. 6D is a conceptual illustration of a modified model-workflow pair 630. Specifically, the model-workflow pair illustration 630 is a modified version of the aggregate model-workflow pair from FIG. 6A. As shown, the modified model-workflow pair illustration 630 includes the original column for model inputs 602 from FIG. 6A and includes modified columns for model calculations 634, model output ranges 636, and workflow operations 638. In this example, the modified predictive model has a single input, data from Sensor A, and has two calculations, Calculations I and III. If the output probability of the modified model is less than 75%, then workflow Operation 1 is performed. If the output probability is between 75% and 85%, then workflow Operation 2 is performed. And if the output probability is greater than 85%, then workflow Operation 3 is performed. Other example modified model-workflow pairs are possible and contemplated herein.

Returning to FIG. 10, at block 1020, the analytics system 108 may then transmit any model and/or workflow modifications to one or more assets. For example, the analytics system 108 may transmit a modified individualized model-workflow pair to the asset 102 (e.g., the asset whose data caused the modification) and a modified aggregate model to the asset 104. In this way, the analytics system 108 may dynamically modify models and/or workflows based on data associated with the operation of the asset 102 and distribute such modifications to multiple assets, such as the fleet to which the asset 102 belongs. Accordingly, other assets may benefit from the data originating from the asset 102 in that the other assets' local model-workflow pairs may be refined based on such data, thereby helping to create more accurate and robust model-workflow pairs F. Dynamic Execution of Model/Workflow In another aspect, the asset 102 and/or the analytics system 108 may be configured to dynamically adjust executing a model-workflow pair. In particular, the asset 102 and/or the analytics system 108 may be configured to detect certain events that trigger a change in responsibilities with respect to whether the asset 102 and/or the analytics system 108 should be executing the predictive model and/or workflow.

In operation, both the asset 102 and the analytics system 108 may execute all or a part of a model-workflow pair on behalf of the asset 102. For example, after the asset 102 receives a model-workflow pair from the analytics system 108, the asset 102 may store the model-workflow pair in data storage but then may rely on the analytics system 108 to centrally execute part or all of the model-workflow pair. In particular, the asset 102 may provide at least sensor and/or actuator data to the analytics system 108, which may then use such data to centrally execute a predictive model for the asset 102. Based on the output of the model, the analytics system 108 may then execute the corresponding workflow or the analytics system 108 may transmit to the asset 102 the output of the model or an instruction for the asset 102 to locally execute the workflow.

In other examples, the analytics system 108 may rely on the asset 102 to locally execute part or all of the model-workflow pair. Specifically, the asset 102 may locally execute part or all of the predictive model and transmit results to the analytics system 108, which may then cause the analytics system 108 to centrally execute the corresponding workflow. Or the asset 102 may also locally execute the corresponding workflow.

In yet other examples, the analytics system 108 and the asset 102 may share in the responsibilities of executing the model-workflow pair. For instance, the analytics system 108 may centrally execute portions of the model and/or workflow, while the asset 102 locally executes the other portions of the model and/or workflow. The asset 102 and analytics system 108 may transmit results from their respective executed responsibilities. Other examples are also possible.

At some point in time, the asset 102 and/or the analytics system 108 may determine that the execution of the model-workflow pair should be adjusted. That is, one or both may determine that the execution responsibilities should be modified. This operation may occur in a variety of manners.

Figure 11:
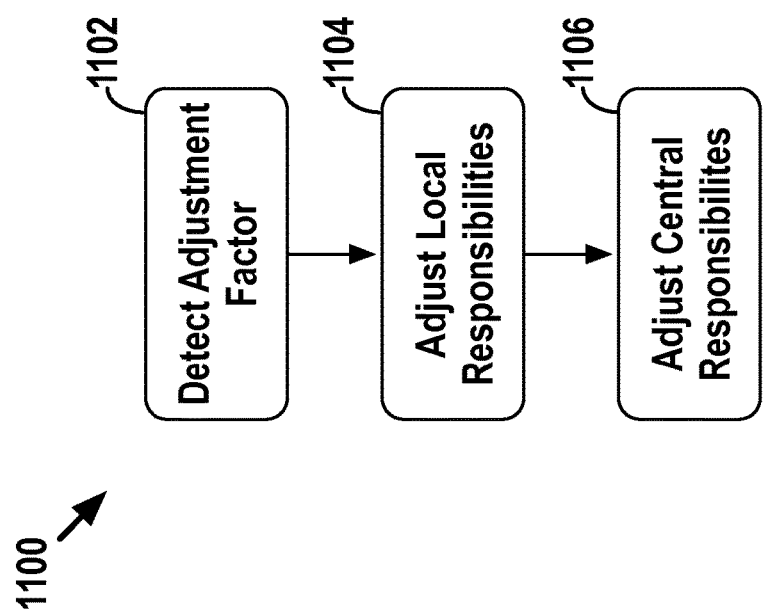
FIG. 11 depicts an example flow diagram of an adjustment phase that may be used for adjusting execution of model-workflow pairs.

FIG. 11 is a flow diagram 1100 depicting one possible example of an adjustment phase that may be used for adjusting execution of a model-workflow pair. For purposes of illustration, the example adjustment phase is described as being carried out by the asset 102 and/or the analytics system 108, but this modification phase may be carried out by other systems as well. One of ordinary skill in the art will appreciate that the flow diagram 1100 is provided for sake of clarity and explanation and that numerous other combinations of operations may be utilized to adjust the execution of a model-workflow pair.

At block 1102, the asset 102 and/or the analytics system 108 may detect an adjustment factor (or potentially multiple) that indicates conditions that require an adjustment to the execution of the model-workflow pair. Examples of such conditions include network conditions of the communication network 106 or processing conditions of the asset 102 and/or analytics system 108, among other examples. Example network conditions may include network latency, network bandwidth, signal strength of a link between the asset 102 and the communication network 106, or some other indication of network performance, among other examples. Example processing conditions may include processing capacity (e.g., available processing power), processing usage (e.g., amount of processing power being consumed) or some other indication of processing capabilities, among other examples.

In practice, detecting an adjustment factor may be performed in a variety of manners. For example, this operation may involve determining whether network (or processing) conditions reach one or more threshold values or whether conditions have changed in a certain manner. Other examples of detecting an adjustment factor are also possible.

In particular, in some cases, detecting an adjustment factor may involve the asset 102 and/or the analytics system 108 detecting an indication that a signal strength of a communication link between the asset 102 and the analytics system 108 is below a threshold signal strength or has been decreasing at a certain rate of change. In this example, the adjustment factor may indicate that the asset 102 is about to go "off-line."

In another case, detecting an adjustment factor may additionally or alternatively involve the asset 102 and/or the analytics system 108 detecting an indication that network latency is above a threshold latency or has been increasing at a certain rate of change. Or the indication may be that a network bandwidth is below a threshold bandwidth or has been decreasing at a certain rate of change. In these examples, the adjustment factor may indicate that the communication network 106 is lagging.

In yet other cases, detecting an adjustment factor may additionally or alternatively involve the asset 102 and/or the analytics system 108 detecting an indication that processing capacity is below a particular threshold or has been decreasing at a certain rate of change and/or that processing usage is above a threshold value or increasing at a certain rate of change. In such examples, the adjustment factor may indicate that processing capabilities of the asset 102 (and/or the analytics system 108) are low. Other examples of detecting an adjustment factor are also possible.

At block 1104, based on the detected adjustment factor, the local execution responsibilities may be adjusted, which may occur in a number of manners. For example, the asset 102 may have detected the adjustment factor and then determined to locally execute the model-workflow pair or a portion thereof. In some cases, the asset 102 may then transmit to the analytics system 108 a notification that the asset 102 is locally executing the predictive model and/or workflow.

In another example, the analytics system 108 may have detected the adjustment factor and then transmitted an instruction to the asset 102 to cause the asset 102 to locally execute the model-workflow pair or a portion thereof. Based on the instruction, the asset 102 may then locally execute the model-workflow pair.

At block 1106, the central execution responsibilities may be adjusted, which may occur in a number of manners. For example, the central execution responsibilities may be adjusted based on the analytics system 108 detecting an indication that the asset 102 is locally executing the predictive model and/or the workflow. The analytics system 108 may detect such an indication in a variety of manners.

In some examples, the analytics system 108 may detect the indication by receiving from the asset 102 a notification that the asset 102 is locally executing the predictive model and/or workflow. The notification may take various forms, such as binary or textual, and may identify the particular predictive model and/or workflow that the asset is locally executing.

In other examples, the analytics system 108 may detect the indication based on received operating data for the asset 102. Specifically, detecting the indication may involve the analytics system 108 receiving operating data for the asset 102 and then detecting one or more characteristics of the received data. From the one or more detected characteristics of the received data, the analytics system 108 may infer that the asset 102 is locally executing the predictive model and/or workflow.

In practice, detecting the one or more characteristics of the received data may be performed in a variety of manners. For instance, the analytics system 108 may detect a type of the received data. In particular, the analytics system 108 may detect a source of the data, such as a particular sensor or actuator that generated sensor or actuator data. Based on the type of the received data, the analytics system 108 may infer that the asset 102 is locally executing the predictive model and/or workflow. For example, based on detecting a sensor-identifier of a particular sensor, the analytics system 108 may infer the that asset 102 is locally executing a predictive model and corresponding workflow that causes the asset 102 to acquire data from the particular sensor and transmit that data to the analytics system 108.

In another instance, the analytics system 108 may detect an amount of the received data. The analytics system 108 may compare that amount to a certain threshold amount of data. Based on the amount reaching the threshold amount, the analytics system 108 may infer that the asset 102 is locally executing a predictive model and/or workflow that causes the asset 102 to acquire an amount of data equivalent to or greater than the threshold amount. Other examples are also possible.

In example implementations, detecting the one or more characteristics of the received data may involve the analytics system 108 detecting a certain change in one or more characteristics of the received data, such as a change in the type of the received data, a change in the amount of data that is received, or change in the frequency at which data is received. In a particular example, a change in the type of the received data may involve the analytics system 108 detecting a change in the source of sensor data that it is receiving (e.g., a change in sensors and/or actuators that are generating the data provided to the analytics system 108).

In some cases, detecting a change in the received data may involve the analytics system 108 comparing recently received data to data received in the past (e.g., an hour, day, week, etc. before a present time). In any event, based on detecting the change in the one or more characteristics of the received data, the analytics system 108 may infer that the asset 102 is locally executing a predictive model and/or workflow that causes such a change to the data provided by the asset 102 to the analytics system 108.

Moreover, the analytics system 108 may detect an indication that the asset 102 is locally executing the predictive model and/or the workflow based on detecting the adjustment factor at block 1102. For example, in the event that the analytics system 108 detects the adjustment factor at block 1102, the analytics system 108 may then transmit to the asset 102 instructions that cause the asset 102 to adjust its local execution responsibilities and accordingly, the analytics system 108 may adjust its own central execution responsibilities. Other examples of detecting the indication are also possible.

In example implementations, the central execution responsibilities may be adjusted in accordance with the adjustment to the local execution responsibilities. For instance, if the asset 102 is now locally executing the predictive model, then the analytics system 108 may accordingly cease centrally executing the predictive model (and may or may not cease centrally executing the corresponding workflow). Further, if the asset 102 is locally executing the corresponding workflow, then the analytics system 108 may accordingly cease executing the workflow (and may or may not cease centrally executing the predictive model). Other examples are also possible.

In practice, the asset 102 and/or the analytics system 108 may continuously perform the operations of blocks 1102-1106. And at times, the local and central execution responsibilities may be adjusted to facilitate optimizing the execution of model-workflow pairs.

Moreover, in some implementations, the asset 102 and/or the analytics system 108 may perform other operations based on detecting an adjustment factor. For example, based on a condition of the communication network 106 (e.g., bandwidth, latency, signal strength, or another indication of network quality), the asset 102 may locally execute a particular workflow. The particular workflow may be provided by the analytics system 108 based on the analytics system 108 detecting the condition of the communication network, may be already stored on the asset 102, or may be a modified version of a workflow already stored on the asset 102 (e.g., the asset 102 may locally modify a workflow). In some cases, the particular workflow may include a data-acquisition scheme that increases or decreases a sampling rate and/or a data-transmission scheme that increases or decreases a transmission rate or amount of data transmitted to the analytics system 108, among other possible workflow operations.

In a particular example, the asset 102 may determine that one or more detected conditions of the communication network have reached respective thresholds (e.g., indicating poor network quality). Based on such a determination, the asset 102 may locally execute a workflow that includes transmitting data according to a data-transmission scheme that reduces the amount and/or frequency of data the asset 102 transmits to the analytics system 108. Other examples are also possible.

V. Example Methods

Figure 12:
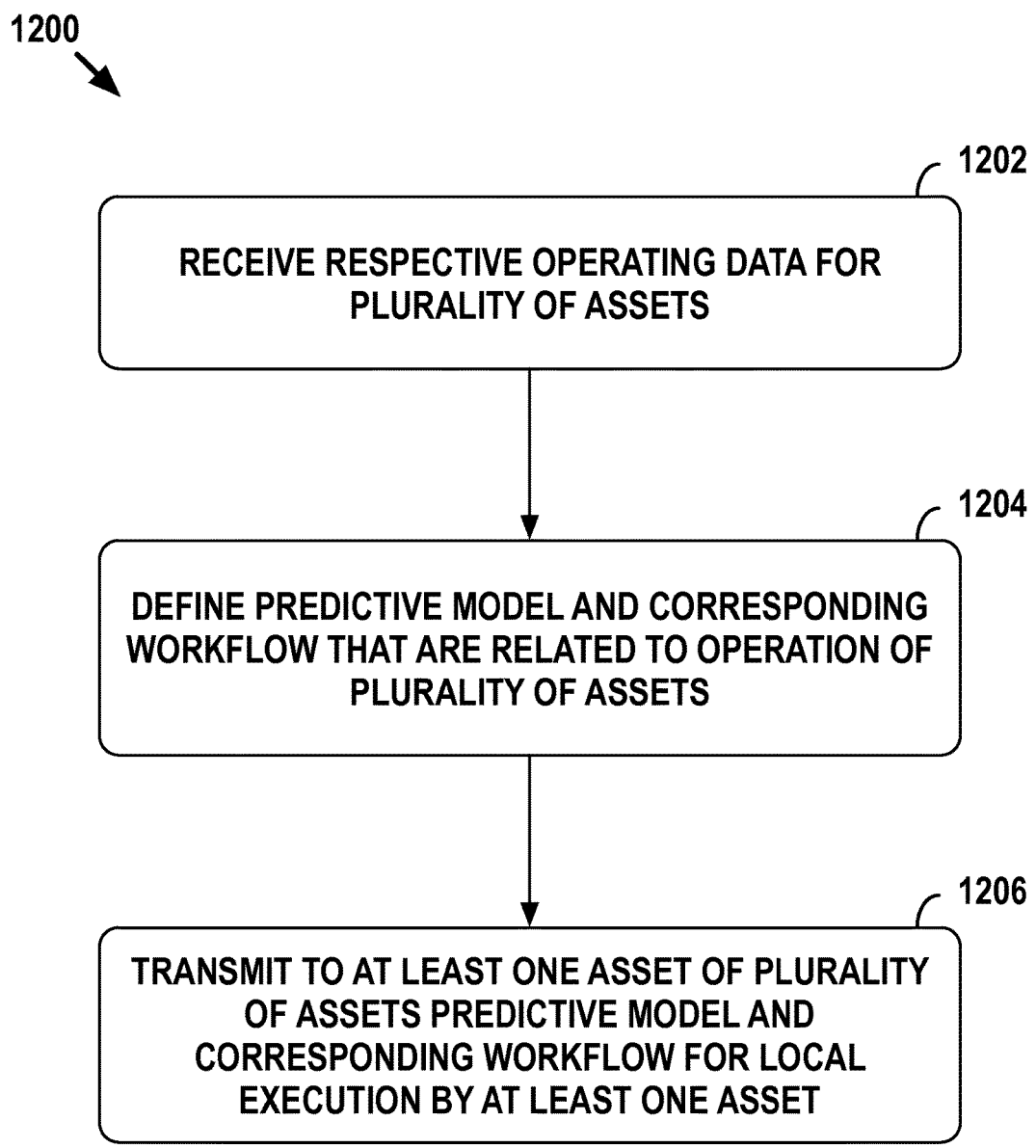
FIG. 12 depicts a flow diagram of an example method for defining and deploying an aggregate, predictive model and corresponding workflow

Turning now to FIG. 12, a flow diagram is depicted illustrating an example method 1200 for defining and deploying an aggregate, predictive model and corresponding workflow that may be performed by the analytics system 108. For the method 1200 and the other methods discussed below, the operations illustrated by the blocks in the flow diagrams may be performed in line with the above discussion. Moreover, one or more operations discussed above may be added to a given flow diagram.

At block 1202, the method 1200 may involve the analytics system 108 receiving respective operating data for a plurality of assets (e.g., the assets 102 and 104). At block 1204, the method 1200 may involve the analytics system 108, based on the received operating data, defining a predictive model and a corresponding workflow (e.g., a failure model and corresponding workflow) that are related to the operation of the plurality of assets. At block 1206, the method 1200 may involve the analytics system 108 transmitting to at least one asset of the plurality of assets (e.g., the asset 102) the predictive model and the corresponding workflow for local execution by the at least one asset.

Figure 13:
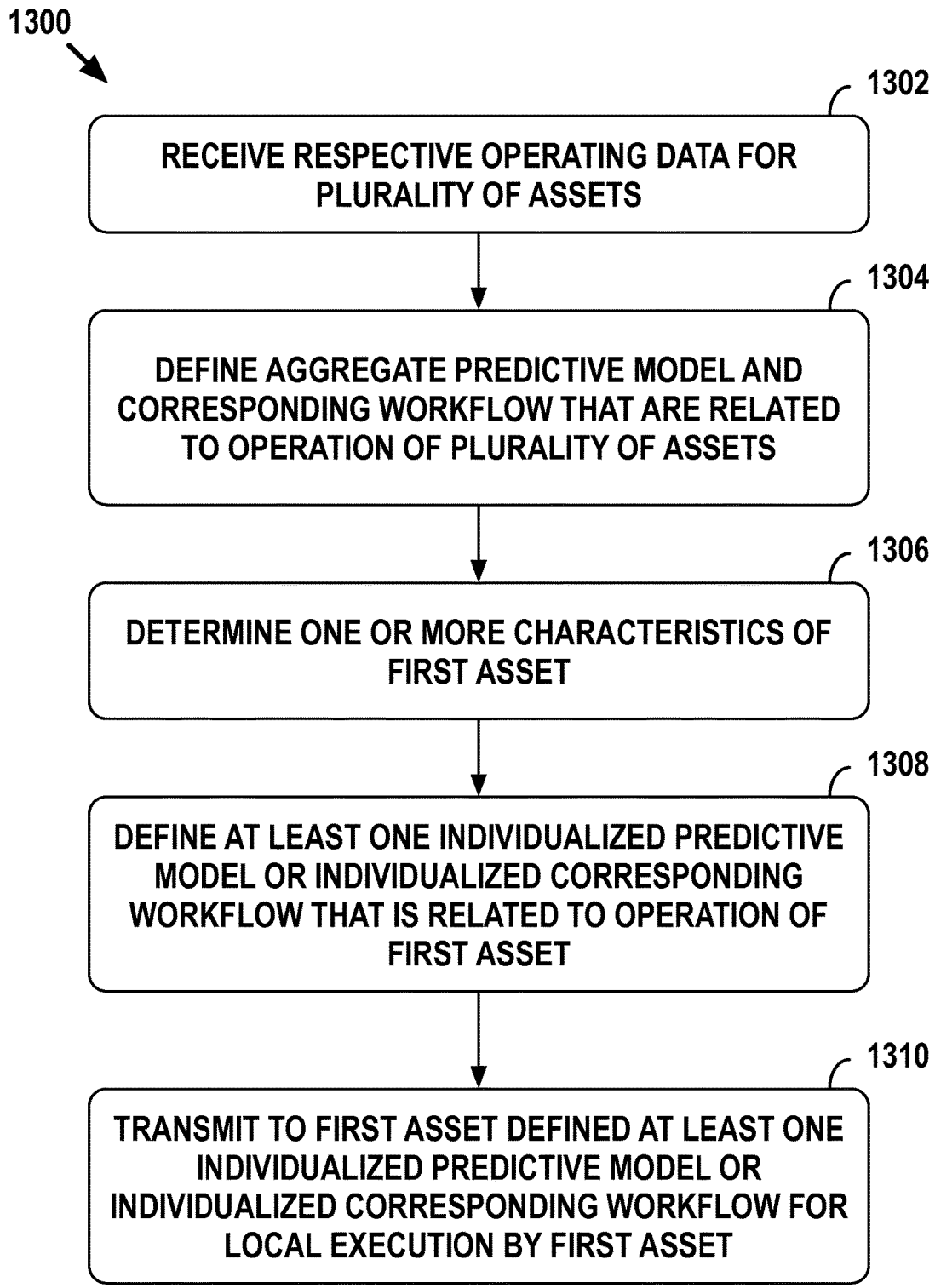
FIG. 13 depicts a flow diagram of an example method for defining and deploying an individualized, predictive model and/or corresponding workflow

FIG. 13 depicts a flow diagram of an example method 1300 for defining and deploying an individualized, predictive model and/or corresponding workflow that may be performed by the analytics system 108. At block 1302, the method 1300 may involve the analytics system 108 receiving operating data for a plurality of assets, where the plurality of assets includes at least a first asset (e.g., the asset 102). At block 1304, the method 1300 may involve the analytics system 108, based on the received operating data, defining an aggregate predictive model and an aggregate corresponding workflow that are related to the operation of the plurality of assets. At block 1306, the method 1300 may involve the analytics system 108 determining one or more characteristics of the first asset. At block 1308, the method 1300 may involve the analytics system 108, based on the one or more characteristics of the first asset and the aggregate predictive model and the aggregate corresponding workflow, defining at least one of an individualized predictive model or an individualized corresponding workflow that is related to the operation of the first asset. At block 1310, the method 1300 may involve the analytics system 108 transmitting to the first asset the defined at least one individualized predictive model or individualized corresponding workflow for local execution by the first asset.

Figure 14:
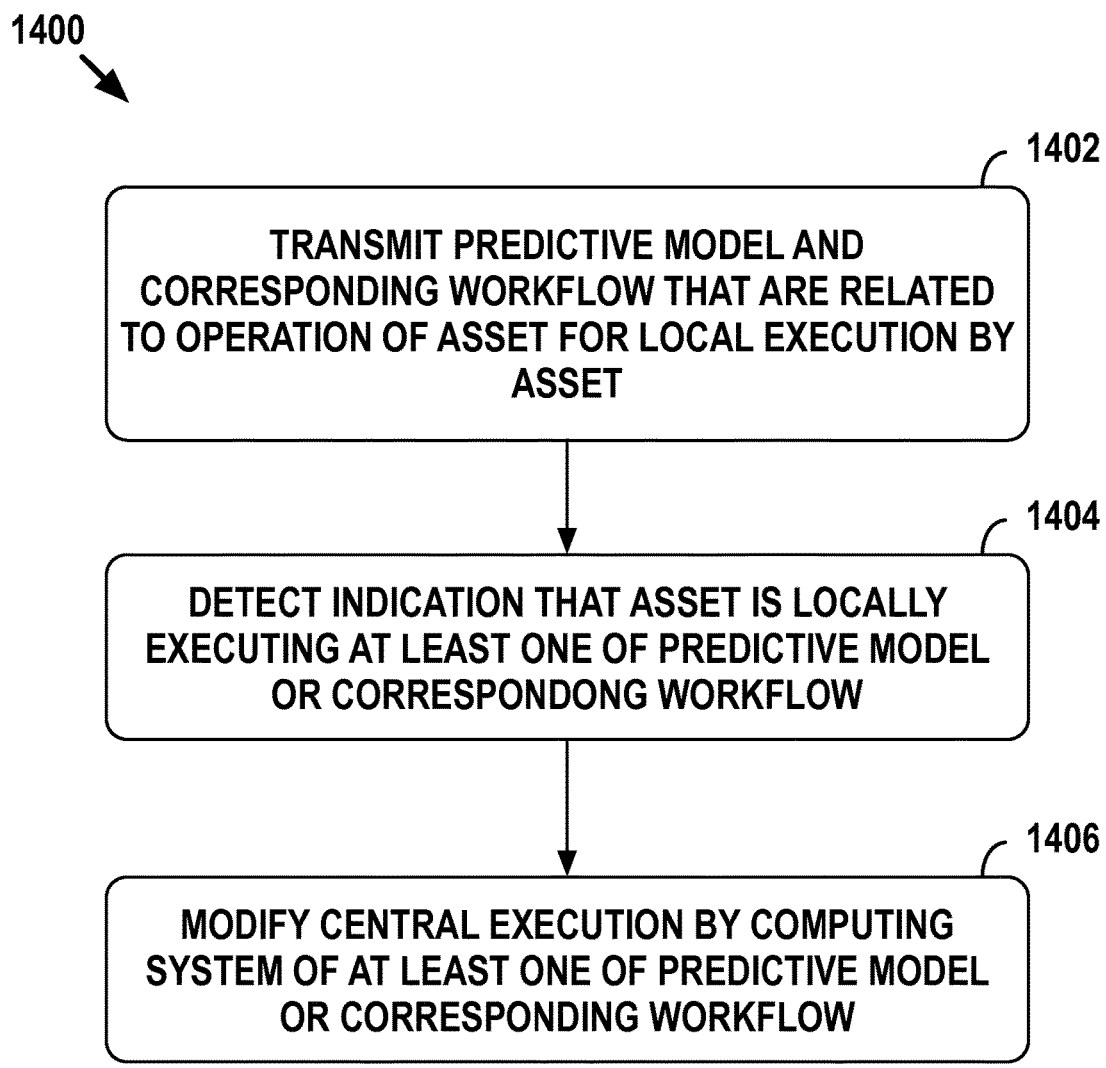
FIG. 14 depicts a flow diagram of an example method for dynamically modifying the execution of model-workflow pairs.

FIG. 14 depicts a flow diagram of an example method 1400 for dynamically modifying the execution of model-workflow pairs that may be performed by the analytics system 108. At block 1402, the method 1400 may involve the analytics system 108 transmitting to an asset (e.g., the asset 102) a predictive model and corresponding workflow that are related to the operation of the asset for local execution by the asset. At block 1404, the method 1400 may involve the analytics system 108 detecting an indication that the asset is locally executing at least one of the predictive model or the corresponding workflow. At block 1406, the method 1400 may involve the analytics system 108, based on the detected indication, modifying central execution by the computing system of at least one of the predictive model or the corresponding workflow.

Similar to method 1400, another method for dynamically modifying the execution of model-workflow pairs may be performed by an asset (e.g., the asset 102). For instance, such a method may involve the asset 102 receiving from a central computing system (e.g., the analytics system 108) a predictive model and corresponding workflow that are related to the operation of the asset 102. The method may also involve the asset 102 detecting an adjustment factor indicating one or more conditions associated with adjusting execution of the predictive model and the corresponding workflow. The method may involve, based on the detected adjustment factor, (i) modifying local execution by the asset 102 of at least one of the predictive model or the corresponding workflow and (ii) transmitting to the central computing system an indication that the asset 102 is locally executing the at least one of the predictive model or the corresponding workflow to facilitate causing the central computing system to modify central execution by the computing system of at least one of the predictive model or the corresponding workflow.

To the extent that examples described herein involve operations performed or initiated by actors, such as "humans", "operators", "users" or other entities, this is for purposes of example and explanation only. The claims should not be construed as requiring action by such actors unless explicitly recited in the claim language.

The invention claimed is:

1. A computing system comprising:
a network interface configured to communicatively couple the computing system via a communication network to assets and local analytics devices located remote from the computing system;
at least one processor;
a non-transitory computer-readable medium; and
program instructions stored on the non-transitory computer-readable medium that are executable by the at least one processor to cause the computing system to:
receive operating data for a plurality of assets, wherein the operating data comprises historical sensor data associated with past occurrences of a given type of failure event at the plurality of assets;
based at least on the received historical sensor data, define (i) a predictive model that is configured to predict occurrences of the given type of failure event and (ii) a corresponding workflow that is configured to run based on an output of the predictive model; and
transmit via the communication network, to at least one particular local analytics device that corresponds to and is located at or near a particular asset, the predictive model and the corresponding workflow and thereby configure the particular local analytics device to (i) locally apply the predictive model to sensor data received from the particular asset without involvement of the computing system and thereby predict occurrences of the given type of failure event and (ii) in response to a predicted occurrence of the given type of failure event, locally execute the corresponding workflow without involvement of the computing system such that one or more operations are initiated at the particular asset.

2. The computing system of claim 1, wherein the operating data further comprises historical abnormal-condition data associated with a failure that occurred at a given asset at a particular time, and wherein the historical sensor data indicates at least one operating condition of the given asset at the particular time.

3. The computing system of claim 1, wherein the predictive model is defined to output a probability that the given type of failure event will occur at a given asset within a period of time into the future.

4. The computing system of claim 3, wherein the corresponding workflow comprises one or more operations to be performed based on the determined probability.

5. The computing system of claim 1, wherein the corresponding workflow comprises a local analytics device corresponding to an asset triggering the asset to control one or more actuators of the asset to facilitate modifying an operating condition of the asset.

6. The computing system of claim 1, wherein the corresponding workflow comprises a local analytics device corresponding to an asset causing one or more diagnostic tools to be executed locally by the asset.

7. The computing system of claim 1, wherein the corresponding workflow comprises a local analytics device corresponding to an asset acquiring sensor data from the asset according to a particular data-acquisition scheme.

8. The computing system of claim 7, wherein the particular data-acquisition scheme indicates one or more sensors of the asset from which data is to be acquired.

9. The computing system of claim 8, wherein the particular data-acquisition scheme further indicates an amount of data that the local analytics device corresponding to the asset is to acquire from each of the one or more sensors of the asset.

10. The computing system of claim 1, wherein the corresponding workflow comprises a local analytics device corresponding to an asset transmitting data related to operation of the asset to the computing system according to a particular data-transmission scheme.

11. The computing system of claim 10, wherein the particular data-transmission scheme indicates a frequency at which the local analytics device corresponding to the asset is to transmit the data related to operation of the asset to the computing system.

12. The computing system of claim 1, wherein the computing system is a first computing system, and wherein the corresponding workflow comprises a local analytics device corresponding to an asset transmitting instructions to a second computing system to facilitate causing the second computing system to carry out an operation related to the asset.

13. The computing system of claim 1, wherein the particular local analytics device that corresponds to the particular asset comprises a first local analytics device that corresponds to a first asset, and wherein transmitting the predictive model and the corresponding workflow to the at least one particular local analytics device comprises transmitting the predictive model and the corresponding workflow to both the first local analytics device and also a second local analytics device that corresponds to and is located at or near a second asset and thereby (a) configuring the first local analytics device to (i) locally apply the predictive model to sensor data received from the first asset without involvement of the computing system and thereby predict occurrences of the given type of failure event at the first asset and (ii) in response to a predicted occurrence of the given type of failure event at the first asset, locally execute the corresponding workflow without involvement of the computing system such that one or more operations are initiated at the first asset, and (b) configuring the second local analytics device to (i) locally apply the predictive model to sensor data received from the second asset without involvement of the computing system and thereby predict occurrences of the given type of failure event at the second asset and (ii) in response to a predicted occurrence of the given type of failure event at the second asset, locally execute the corresponding workflow without involvement of the computing system such that one or more operations are initiated at the second asset.

14. A non-transitory computer-readable medium having instructions stored thereon that are executable to cause a computing system comprising a network interface configured to communicatively couple the computing system via a communication network to assets and local analytics devices located remote from the computing system to:
receive operating data for a plurality of assets, wherein the operating data comprises historical sensor data associated with past occurrences of a given type of failure event at the plurality of assets;
based at least on the received historical sensor data, define (i) a predictive model that is configured to predict occurrences of the given type of failure event and (ii) a corresponding workflow that is configured to run based on an output of the predictive model; and
transmit via the communication network, to at least one particular local analytics device that corresponds to and is located at or near a particular asset, the predictive model and the corresponding workflow and thereby configure the particular local analytics device to (i) locally apply the predictive model to sensor data received from the particular asset without involvement of the computing system and thereby predict occurrences of the given type of failure event and (ii) in response to a predicted occurrence of the given type of failure event, locally execute the corresponding workflow without involvement of the computing system such that one or more operations are initiated at the particular asset.

15. The non-transitory computer-readable medium of claim 14, wherein the predictive model is defined to output a probability that the given type of failure event will occur at a given asset within a period of time into the future.

16. The non-transitory computer-readable medium of claim 14, wherein the corresponding workflow comprises a local analytics device corresponding to an asset triggering the asset to control one or more actuators of the asset to facilitate modifying an operating condition of the asset.

17. The non-transitory computer-readable medium of claim 14, wherein the corresponding workflow comprises a local analytics device corresponding to an asset causing one or more diagnostic tools to be executed locally by the asset.

18. The non-transitory computer-readable medium of claim 14, wherein the computing system is a first computing system, and wherein the corresponding workflow comprises a local analytics device corresponding to an asset transmitting instructions to a second computing system to facilitate causing the second computing system to carry out an operation related to the asset.

19. A computer-implemented method performed by a computing system configured to be communicatively coupled via a communication network to assets and local analytics devices located remote from the computing system, the method comprising:
receiving operating data for a plurality of assets, wherein the operating data comprises historical sensor data associated with past occurrences of a given type of failure event at the plurality of assets;
based at least on the received historical sensor data, defining (i) a predictive model that is configured to predict occurrences of the given type of failure event and (ii) a corresponding workflow that is configured to run based on an output of the predictive model; and
transmitting via the communication network, to at least one particular local analytics device that corresponds to and is located at or near a particular asset, the predictive model and the corresponding workflow and thereby configuring the particular local analytics device to (i) locally apply the predictive model to sensor data received from the particular asset without involvement of the computing system and thereby predict occurrences of the given type of failure event and (ii) in response to a predicted occurrence of the given type of failure event, locally execute the corresponding workflow without involvement of the computing system such that one or more operations are initiated at the particular asset.

20. The computer-implemented method of claim 19, wherein the corresponding workflow comprises a local analytics device corresponding to an asset acquiring sensor data from the asset according to a particular data-acquisition scheme, and wherein the particular data-acquisition scheme indicates one or more sensors of the asset from which data is to be acquired.

* * * * *